United States Patent
Bradley et al.

(10) Patent No.: US 12,037,578 B2
(45) Date of Patent: Jul. 16, 2024

(54) METHODS FOR ISOLATING DNA FROM A BLOOD SAMPLE

(71) Applicant: BioCaptiva Limited, Fife (GB)

(72) Inventors: Mark Bradley, Edinburgh Lothian (GB); Matthew Owens, Edinburgh Lothian (GB)

(73) Assignee: BIOCAPTIVA LIMITED, Fife (GB)

( * ) Notice: Subject to any disclaimer, the term of this patent is extended or adjusted under 35 U.S.C. 154(b) by 946 days.

(21) Appl. No.: 16/761,465

(22) PCT Filed: Nov. 14, 2018

(86) PCT No.: PCT/GB2018/053304
§ 371 (c)(1),
(2) Date: May 4, 2020

(87) PCT Pub. No.: WO2019/097232
PCT Pub. Date: May 23, 2019

(65) Prior Publication Data
US 2020/0392480 A1    Dec. 17, 2020

(30) Foreign Application Priority Data
Nov. 14, 2017 (GB) .................................... 1718802

(51) Int. Cl.
| | | |
|---|---|---|
| *C12N 15/10* | (2006.01) | |
| *C08F 220/14* | (2006.01) | |
| *C08F 220/54* | (2006.01) | |
| *C12Q 1/6869* | (2018.01) | |

(52) U.S. Cl.
CPC ........ *C12N 15/1006* (2013.01); *C08F 220/14* (2013.01); *C08F 220/54* (2013.01); *C12Q 1/6869* (2013.01); *C08F 2438/03* (2013.01); *C08F 2500/04* (2013.01); *C12N 2310/10* (2013.01); *C12N 2320/10* (2013.01); *C12N 2330/10* (2013.01); *C12Q 2560/00* (2013.01); *C12Q 2600/00* (2013.01)

(58) Field of Classification Search
CPC ............ C12N 15/1006; C12N 2310/10; C12N 2320/10; C12N 2330/10; C08F 220/14; C08F 220/54; C08F 2438/03; C08F 2500/04; C12Q 1/6869; C12Q 2560/00; C12Q 2600/00
USPC ....................................................... 536/25.4
See application file for complete search history.

(56) References Cited

U.S. PATENT DOCUMENTS

2012/0024779 A1 * 2/2012 Ochiai ................... B01D 29/00
                                                                524/558
2017/0283788 A1   10/2017 Khoja et al.

FOREIGN PATENT DOCUMENTS

| WO | WO 02/10182 A2 | 2/2002 |
| WO | WO 2019/053243 A1 | 3/2019 |

OTHER PUBLICATIONS

Kita et al. Functional Monomers and Polymers. LXI. Photochemical Reactions on the Synthetic Polymers Containing Thymine Bases. Journal of Polymer Science: Polymer Chemistry Edition, vol. 18,427-439 (1980) (Year: 1980).*
Liu et al. Development of thermosensitive copolymers of poly(2-methoxyethyl acrylateco-poly(ethylene glycol) methyl ether acrylate) and their nanogels synthesized by RAFT dispersion polymerization in water. Polym. Chem., 2012, 3, 504-513. (Year: 2012).*
Liu et al., "Water-soluble clickable nucleic acid (CNA) polymer synthesis by functionalizing the pendant hydroxyl," Chem. Commun., 53(73):10156-10159, (2017).
Van Der AA, Eveline M., *Synthesis and Characterization of Nucleobase-Containing Polyelectrolytes for Gene Delivery*, MS Thesis, Virginia Polytechnic Institute and State University (Blacksburg, VA), pp. 1-84, (2010).
Zhang et al., "Nucleobase-functionalized acrylic ABA triblock copolymers and supramolecular blends," Polymer Chemistry, 6(13): 2434-2444, (2015).
International Search Report and Written Opinion of the International Searching Authority for International Application No. PCT/GB2018/053304, dated Jan. 31, 2019.
Kang et al., "Exploiting nucleobase-containing materials—from monomers to complex morphologies using RAFT dispersion polymerization," Polymer Chemistry, 6:106-117, (2015).
Kang et al., "Use of complementary nucleobase-containing synthetic polymers to prepare complex self-assembled morphologies in water," Polymer Chemistry, 7:2836-2846, (2016).
Spijker et al., "Synthesis and Assembly Behavior of Nucleobase-Functionalized Block Copolymers," Journal of Polymer Science Part A: Polymer Chemistry, 44(13):4242-4250, (2006).
Spijker et al., "Atom Transfer Radical Polymerization of Adenine, Thymine, Cytosine, and Guanine Nucleobase Monomers," Macromolecules, 40:12-18, (2007).
EP Communication pursuant to Article 94(3) for EP Application No. 18822113.9, mailed May 22, 2024.

* cited by examiner

Primary Examiner — Yih-Horng Shiao
(74) Attorney, Agent, or Firm — Alston & Bird LLP

(57) ABSTRACT

The present invention relates to methods for isolating nucleic acids present in a sample, in particular cell-free DNA (cfDNA) from a blood sample and polymers, substrates and kits for the method. Polymers with characteristics suitable to bind such nucleic acids are provided.

18 Claims, 17 Drawing Sheets

Figure 10

Figure 1:
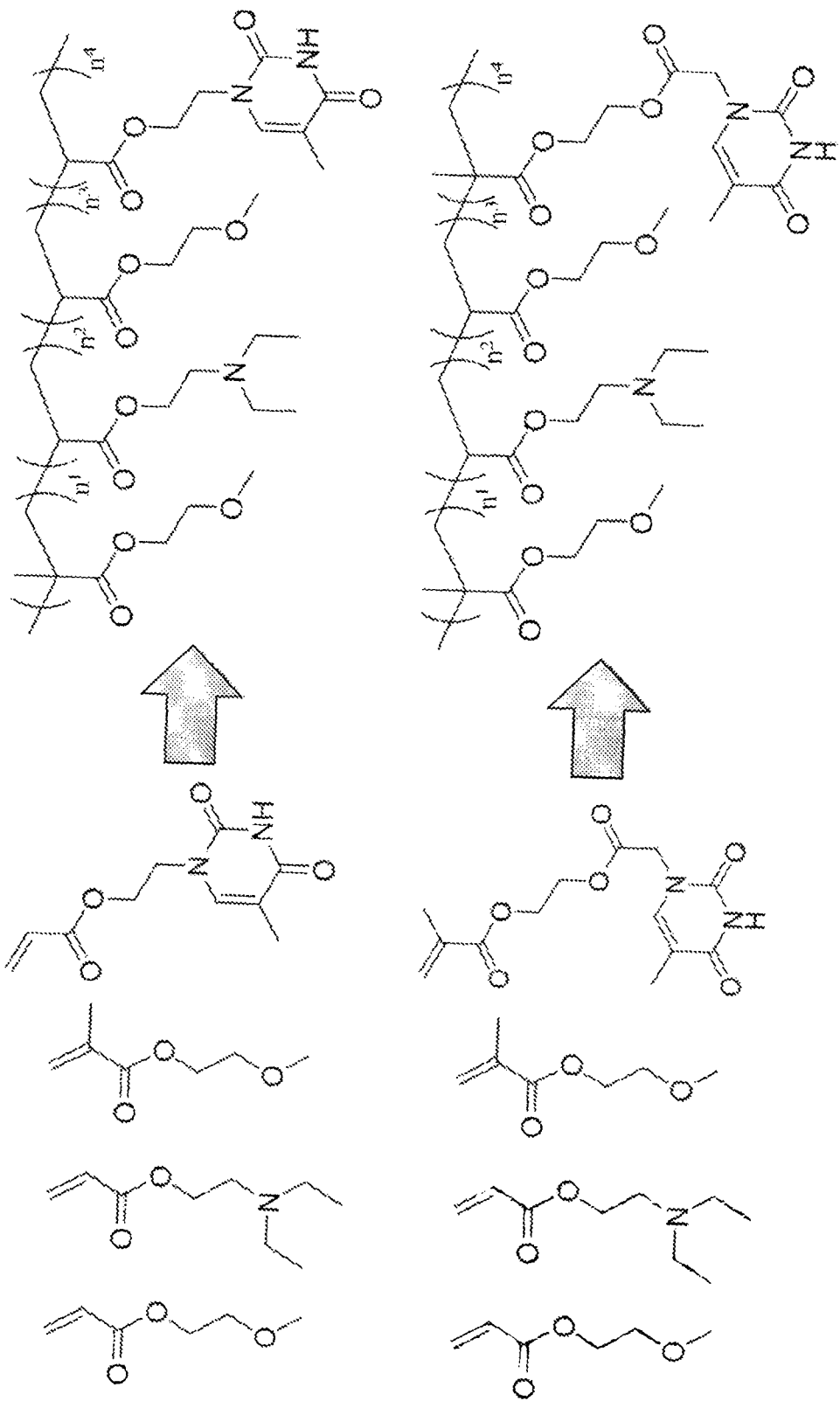

|      | MEMA (%) | DEAEA (%) | MEA (%) | ThEA (%) | ThAcMA (%) | PEGA (%) |
|------|----------|-----------|---------|----------|------------|----------|
| Ms13 | 39       | 32        | 29      | -        | -          | -        |
| Ms22 | 38       | 27        | 29      | 6        | -          | -        |
| Ms23 | 37       | 26        | 28      | -        | 9          | -        |
| Ms26 | 42       | 25        | 32      | 1        | -          | -        |
| Ms27 | 38       | 26        | 28      | 8        | -          | -        |
| Ms28 | 39       | 28        | 29      | -        | 4          | -        |
| Ms29 | 33       | 28        | 25      | -        | 14         | -        |
| MsY  | 39       | 30        | 29      | 1        | -          | 1        |
| MsX  | 47       | 15        | 36      | 1        | -          | 1        |

MEMA = 2-methoxyethyl methacrylate
DEAEA = diethylamino ethyl acrylate
MEA = 2-methoxyethyl acrylate
ThEA = thymine ethyl acrylate
ThAcMA = thymine acetoxyethyl methacrylate
PEGA = Poly(ethylene glycol) methyl ether acrylate, Mn ~480

Figure 12
A
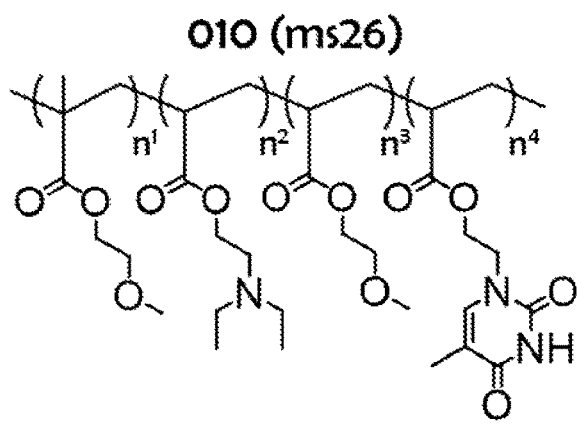
B
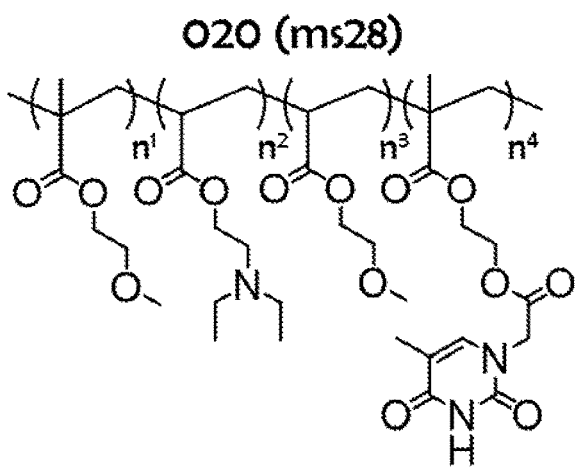
C
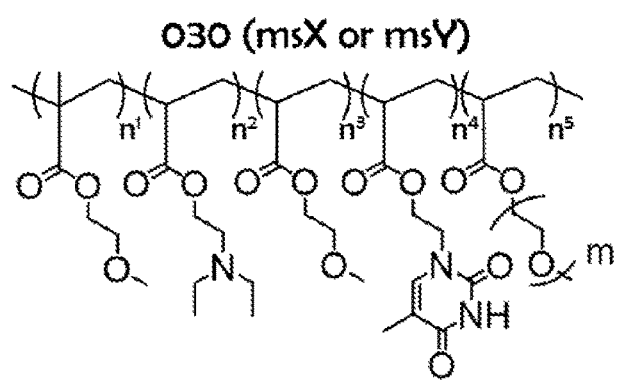
D
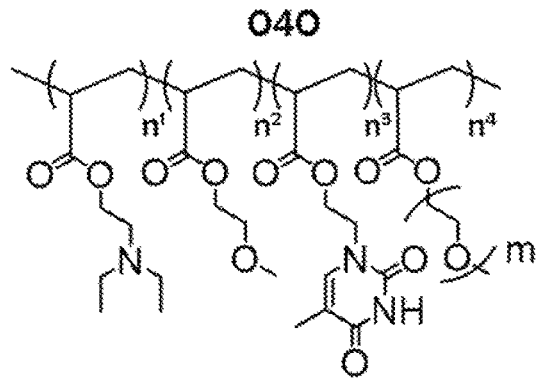

Figure 13

Ms26

|  | 5% | 2% | 0.5% | 0.1% | 0%/THF |
|---|---|---|---|---|---|
| Heparin (1.5 U/mL) | +++ | ++ | ++ | - | - |
| Citrate (11 mM) | - | - | - | - | - |

MsY

|  | 5% | 2% | 0.5% | 0.1% | 0%/THF |
|---|---|---|---|---|---|
| Heparin (1.5 U/mL) | ++ | ++ | + | - | - |
| Citrate (11 mM) | - | - | - | - | - |

MsX

|  | 5% | 2% | 0.5% | 0.1% | 0%/THF |
|---|---|---|---|---|---|
| Heparin (1.5 U/mL) | - | - | - | - | - |
| Citrate (11 mM) | - | - | - | - | - |

METHODS FOR ISOLATING DNA FROM A BLOOD SAMPLE

CROSS-REFERENCE TO RELATED APPLICATIONS

This application is a national stage entry of PCT/GB2018/053304, filed Nov. 14, 2018, which claims the benefit of GB Application No. 1718802.0, filed Nov. 14, 2017, herein incorporated by reference in its entirety for all purposes.

FIELD OF THE INVENTION

The present invention relates to methods for isolating nucleic acids present in a sample, suitably cell-free DNA (cfDNA) from a blood sample and polymers, substrates and kits to allow the method.

BACKGROUND OF THE INVENTION

The ability to sequence circulating small fragment DNA would be a powerful adjuvant to therapy and diagnosis, however cfDNA is at a very low concentration in whole blood. Typically, cfDNA is extracted from a blood draw (venesection), but this provides a very limited quantity of material for biological analysis. A whole blood sample collected from a subject may contain only a very limited amount of cfDNA per millilitre. Thus to obtain sufficient cfDNA for analysis, highly efficient DNA isolation methods must be employed. Accordingly, a continuing need exists for methods of processing whole blood for effective isolation of cfDNA.

SUMMARY OF THE INVENTION

The current invention provides a nucleobase-containing polymer capable of binding to nucleic acids, in particular cfDNA, directly from whole blood. This allows a method to capture increased amounts of cfDNA from blood, for example to allow isolation of cfDNA from blood as part of an apheresis method. Suitably the polymer may be biocompatible, for example such that non-platelet activation or minimal activation is provided. In a method to isolate cfDNA from whole blood, the polymer may be provided to a sample comprising the nucleic acid to be isolated, for example a blood sample or volume comprising cfDNA, by being, for example forming a sponge or filter, or coated onto sponges or filters and integrated in extracorporeal systems and devices. Such a method and systems suitably provide for nucleic acid collection from up to the entire blood volume without significantly removing any other component from the blood. The polymer may then be washed to remove other blood components while retaining the nucleic acid, in particular cfDNA. Suitably, nucleic acid, for example cfDNA may be eluted from the polymer, permitting isolation and concentration of the nucleic acid, for example cfDNA. Recovery of increased quantities of cfDNA may allow enhanced performance of current molecular biological assays by providing sufficient material for comprehensive analyses and experimental replicates, resulting in more extensive experimentation and fewer false results. Additionally, the generation of new assays currently limited by DNA input could be explored such as those focusing on epigenetics, aneuploidy, or mitochondrial DNA.

a. Accordingly a first aspect of the present invention provides a method for the isolation of nucleic acid from a sample, the method comprising the steps; providing a sample comprising nucleic acids to be isolated to a nucleobase containing polymer wherein the polymer further comprises positively charged moieties at physiological pH adapted to electrostatically interact with nucleic acid, b. binding the nucleic acids to be isolated to the polymer.

Suitably the method comprises:

providing a sample comprising nucleic acids to be isolated to a nucleobase containing polymer, and optionally eluting the nucleic acid from the nucleobase containing polymer wherein the nucleobase containing polymer comprises a polymer backbone and at least a proportion of nucleobase based side chains selected from one or more of the following: adenine (A), cytosine (C), guanine (G), thymine (T), uracil (U) or a derivative thereof or combinations thereof. Suitably the polymer backbone comprises diethylamine side chains which can provide a positive charge. Without wishing to be bound by theory the positive charge can aid binding of nucleic acid by the polymer. Suitably a derivative of adenine, cytosine, guanine, thymine or uracil may be an unnatural nucleobase or a modified nucleobase wherein the modification allows interaction with nucleic acid via hydrogen and/or electrostatic binding. Suitably side chains of the polymer backbone may comprise one or more of the following: amines, amides, alcohols, carboxylic acids, alkanes, alkenes, alkynes, esters, ethers, epoxies, sulfonyl hydrides, sulfonyls, thiols, heterocycles, homocycles, aromatic cycles, anti-aromatic cycles, or derivatives thereof, or combinations thereof. Suitably the proportion of side chains of the polymer comprising a nucleobase may be at least 1%, at least 5%, at least 10%, at least 15%, at least 20%. Suitably, the nucleobase based side chains may be ordered, randomised or semi-randomised within the polymer. Suitably nucleobase containing monomers which form the polymer are connected to each other by linkages which permit the linked monomers to form a polymer which provides for base-pairing of nucleic acid. Suitably the sample is provided to the nucleobase containing polymer under conditions as would be understood in the art which allow binding of the nucleic acid to the polymer. Suitably such conditions may be incubation of the sample and the polymer, for example incubation at a temperature in the range 4 to 40 degrees C., suitably between 20 to 40 degrees C., suitably 30 to 40 degrees C., suitably 37 degrees C. Suitably incubation may be provided by flowing of the sample over the polymer, for example the sample may be flowed over the polymer at flow rates of about 20 ml to 50 ml per min, suitably 30 ml/min. Incubation may be for the time taken for the sample to pass over the polymer, up to a 10 s, up to 20 s, up to a 1 min, for example up to 30 minutes, or longer. Suitably elution of the nucleic acid from the polymer may be provided using conditions as would be understood in the art, for example a temperature to disrupt interactions, increased salt concentration, increased ionic strength of solution (e.g. 0.1M Tris HCl, pH8.5, 1.25 NaCl, detergent) (e.g. 0.15% Triton X-100) or pH variation (basic pH), for example suitably elution may be provided using an elution solution. Without wishing to be bound by theory, a suitable incubation solution may be whole blood. Suitably isolation may be immobilisation of the nucleic acids onto the polymer or to a substrate onto which the polymer is provided. Suitably the polymer may be synthesised from monomers comprising either acrylates, methacrylates, acrylamides, methacrylamides, or a combination thereof Suitably a nucleobase enables base-pairing of the polymer to a nucleic acid, for example base-pairing to a nucleic acid. Suitably a nucleobase may allow base pairing via hydrogen bonding with additional electrostatic bonding, for example double or triple hydrogen bonding, for example between amine and carbonyl groups provided on the nucleic acid and the polymer, and electrostatic interactions, for example via tertiary ammonium ions and phosphate esters. Suitably a nucleobase may be a modified purine nucleobase or modified pyrimidine nucleobase wherein the modified purine or pyrimidine nucleobase is based on a modified adenosine or guanosine structure or a modified cytosine, thymine or uridine structure respectively. Nucleobases are well known in the art and have been used for example in fluorescent probes, anticancer agents and antiviral agents.

Suitably the polymer can contain a number of positively charged moieties at physiological pH. Suitably the positively charged moieties enable electrostatic interaction to a nucleic acid. Without wishing to be bound by theory, the positively charged moieties on the polymer may electrostatically attract negatively charged phosphate groups on nucleic acids. Suitably a positively charged moiety may be a protonatable and deprotonatable moiety. Suitably a positively charged moiety may be quaternised. Suitably a positively charged moiety may be diethyl amine.

Suitably the nucleobase based side chains may comprise a fused-ring skeletal structure derived of purine or pyrimidine or a combination of these. Suitably the nucleobase-based side chains may comprise a nucleobase selected from adenine (A), cytosine (C), guanine (G), thymine (T), uracil (U) or a derivative thereof and combinations thereof. For example, a suitable nucleobase derivative may comprise hypoxanthine, xanthine, 7-methylguanine, 5,6, dihydrouracil, 5-methyl cytosine, 5-hydroxymethylcytosine, 3-Nitropyrrole, 5-Nitroindole, 2,6-diaminopurine, 6, 8 diaminopurine, pyrene or a combination thereof.

Suitably the nucleobase side chains may comprise cytosine or thymine or a combination of cytosine and thymine. Suitably a polymer for use in the method may be synthesised from monomers comprising either acrylates and/or methacrylates using acrylate polymerisation chemistry and/or acrylamides. Suitably diethylamine side chains may be provided to provide the polymer with positive charge which can allow electrostatic interaction with the nucleic acid. A number of methods of acrylate polymerisation chemistry exist. Suitably, the synthesis of the nucleobase containing terpolymers (composed of three monomers) or tetrapolymers (composed of four monomers) or pentapolymers (composed of five monomers) or polymers of more than five monomers may be by RAFT polymerisation. Suitably the nucleobase-based monomers may be either or both thymine ethylacrylate or thymine acetoxylethyl methacrylate.

Suitably, the polymer backbone may be synthesised from monomers based on 2-methoxyethyl acrylate/methacrylate, diethylamino ethylacrylate, 2-methoxyethyl acrylate, 2-methoxyethyl methacrylate, diethylamino ethylacrylate, diethylamino ethyl methacrylate, hydroxyethyl acrylate, hydroxyethyl methacrylate, methyl methacrylate, methyl acrylate, styrene, methyl styrene, glycidyl acrylate, glycidyl methacrylate, N-vinylacetamide, 2-methyl-2-nitropropyl methacrylate, acrylic acid, methacrylic acid, 2-[[(butylamino)carbonyl]oxy] ethylacrylate, dimethylamino ethyl acrylate, dimethylamino ethyl methacrylate, mono-2-(acryloyloxy)ethyl succinate, poly(ethylene glycol) methyl ether acrylate/methacrylate or combinations thereof. Suitably monomers of different molecular weights may be provided to form the polymer. Suitably the polymers may be composed of at least two types of monomers. Suitably these different monomers may be of different molecular weights. Suitably monomers of poly(ethylene glycol) methyl ether acrylate/methacrylate may be provided with different or a range of molecular weights Suitably the polymers may be terpolymers or tetrapolymers or pentapolymers. Suitably the polymer backbone may be synthesised using at least 5%, at least 8%, at least 10% of diethylaminoethylacrylate.

Suitably the polymer may be synthesised from acrylate/methacrylate-based monomers. Advantageously polymers formed from acrylate/methacrylate-based monomers with nucleobase side chains, and side chains selected from MEA, MEMA and PEGA side chains have been determined to resist biofouling. Suitably the monomers may comprise a methacryloyl-type monomer.

Suitably the polymer may be synthesised comprising or consisting at least one monomer selected from about 0-50% 2-methoxyethyl acrylate, about 0-50% 2-methoxyethyl methacrylate, about 0-50% diethylamino ethyl acrylate, in combination with at least one monomer selected from about 0-50% thymine ethyl acrylate, and about 0-50% thymine acetoxylethyl methacrylate. Suitably the polymers may provide the monomers in a randomised or semi-randomised sequence.

Suitably the polymer may be synthesised comprising or consisting at least one monomer selected from about 0-50% 2-methoxyethyl acrylate, about 0-50% 2-methoxyethyl methacrylate, about 0-50% diethylamino ethyl acrylate, about 0-50% poly(ethylene glycol) methyl ether acrylate in combination with at least one monomer selected from about 0-50% thymine ethyl acrylate, and about 0-50% thymine acetoxylethyl methacrylate. Suitably the polymers may provide the monomers in a randomised or semi-randomised sequence.

Suitably the polymer may be synthesised comprising or consisting at least one monomer selected from about 10-50% 2-methoxyethyl acrylate, about 0-40% 2-methoxyethyl methacrylate, about 1-40% diethylamino ethyl acrylate, in combination with at least one monomer selected from about 0-25% thymine ethyl acrylate, and about 0-25% thymine acetoxylethyl methacrylate. Suitably the polymers may comprise a randomised or semi-randomised sequence of such monomers.

Suitably the polymer may be synthesised comprising or consisting at least one monomer selected from about 10-50% 2-methoxyethyl acrylate, about 0-40% 2-methoxyethyl methacrylate, about 1-40% diethylamino ethyl acrylate, about 0-25% poly(ethylene glycol) methyl ether acrylate, in combination with at least one monomer selected from about 0-25% thymine ethyl acrylate, and about 0-25% thymine acetoxylethyl methacrylate. Suitably the polymers may comprise a randomised or semi-randomised sequence of such monomers.

Suitably the polymer may be synthesised comprising or consisting at least one monomer selected from about 30-50% 2-methoxyethyl acrylate, about 10-30% 2-methoxyethyl methacrylate, about 25-45% diethylamino ethyl acrylate, in combination with at least one monomer selected from about 0-15% thymine ethyl acrylate, and about 0-15% thymine acetoxylethyl methacrylate. Suitably the polymers may comprise arandomised or semi-randomised sequence of such monomers.

Suitably the polymer may be synthesised comprising or consisting at least one monomer selected from about 30-50% 2-methoxyethyl acrylate, about 20-40% 2-methoxyethyl methacrylate, about 20-40% diethylamino ethyl acrylate, about 0-15% poly(ethylene glycol) methyl ether acrylate, in combination with at least one monomer from about 0-15% thymine ethyl acrylate, and about 0-15% thymine acetoxylethyl methacrylate. Suitably the polymers may comprise a randomised or semi-randomised sequence of such monomers.

Suitable the polymer may be synthesised comprising or consisting monomers of about 18% 2-methoxyethyl methacrylate; about 35% diethylamino ethyl acrylate, about 42% 2-methoxyethyl acrylate, and about 5% thymine ethyl acrylate or thymine acetoxyethyl methacrylate.

Suitable the polymer may be synthesised comprising or consisting monomers of about 39% 2-methoxyethyl methacrylate; about 30% diethylamino ethyl acrylate, about 30% 2-methoxyethyl acrylate, about 1% poly(ethylene glycol) methyl ether acrylate, and about 1% thymine ethyl acrylate or thymine acetoxyethyl methacrylate.

Suitably a polymer may comprise or consist:
2-methoxyethyl methacrylate—47%
Diethylamino ethyl acrylate—15%
2-methoxyethyl acrylate—36%
Thymine ethyl acrylate—1%
Poly(ethylene glycol) methyl ether acrylate Mn 480-1%.

Advantageously, it is considered this polymer demonstrates improved haemocompatibility characteristics.

As will be understood, wherein only one polymer is provided from the lists following at least one polymer noted herein greater than 0%, for example 1% should be provided. Suitably at least 1-50%, at least 5%, at least 10%, at least 15%, at least 20%, at least 25%, at least 30%, at least 40%, at least 45%, at least 50% is provided.

In embodiments the polymer (such as ms26, ms28 or msX) may be provided by:

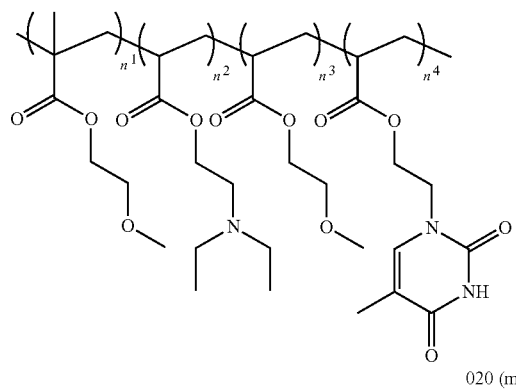

010 (ms26)

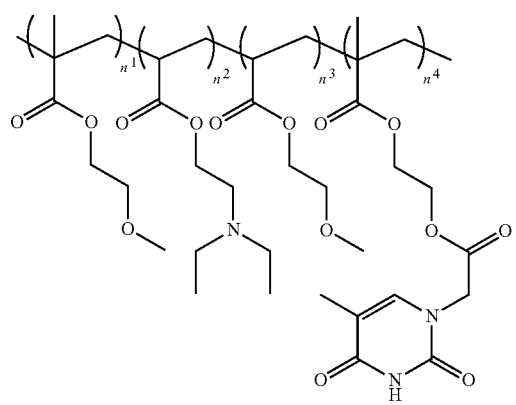

020 (ms28)

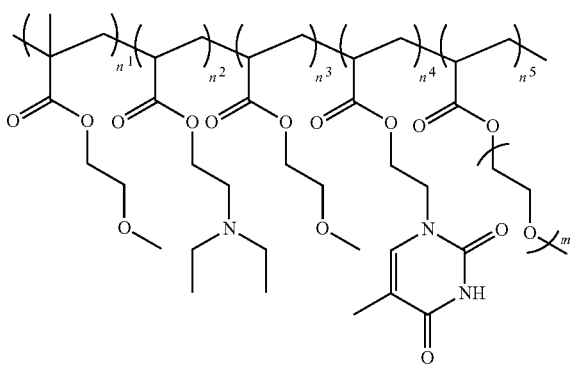

030 (msX or msY)

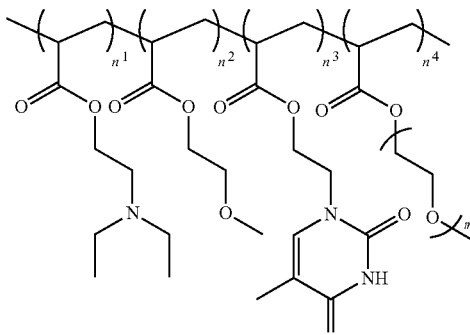

040

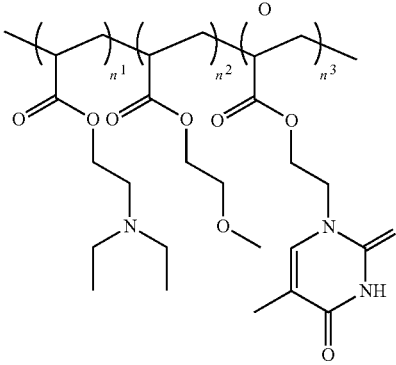

or

Suitably a polymer may be provided having a proportion of monomers as set out in Table 1.

TABLE 1

| | MEMA (%) | DEAEA (%) | MEA (%) | ThEA (%) | ThAcMA (%) | PEGA (%) |
|---|---|---|---|---|---|---|
| Ms13 | 39 | 32 | 29 | — | — | — |
| Ms22 | 38 | 27 | 29 | 6 | — | — |
| Ms23 | 37 | 26 | 28 | — | 9 | — |
| Ms26 | 42 | 25 | 32 | 1 | — | — |
| Ms27 | 38 | 26 | 28 | 8 | — | — |
| Ms28 | 39 | 28 | 29 | — | 4 | — |
| Ms29 | 33 | 28 | 25 | — | 14 | — |
| MsY | 39 | 30 | 29 | 1 | — | 1 |
| MsX | 47 | 15 | 36 | 1 | — | 1 |

Those of skill in the art will appreciate that $n^1$, $n^2$, $n^3$, $n^4$, or $n^5$ may be suitably selected to provide a % composition as discussed herein. These are based on H-NMR data. The percentages refer to the integration/proportion of signal from each of the monomers as part of the polymer signal as a whole.

Proportions of monomers that may be used in the synthesis of the polymers of Table 1 are provided in Table A. As will be appreciated, the percentage of monomers used the preparation may be different to the proportion determined in the polymer synthesised by the monomers.

TABLE A

| | MEMA (%) | DEAEA (%) | MEA (%) | ThEA (%) | ThAcMA (%) | PEGA (%) |
|---|---|---|---|---|---|---|
| Ms13 | 40 | 30 | 30 | — | — | — |
| Ms22 | 38 | 28.5 | 28.5 | 5 | — | — |
| Ms23 | 38 | 28.5 | 28.5 | — | 5 | — |
| Ms26 | 39 | 30 | 30 | 1 | — | — |
| Ms27 | 36 | 27 | 27 | 10 | — | — |
| Ms28 | 39 | 30 | 30 | — | 1 | — |
| Ms29 | 36 | 27 | 27 | — | 10 | — |
| MsY | 38.5 | 30 | 29.5 | 1 | — | 1 |
| MsX | 51 | 10 | 37 | 1 | — | 1 | wherein
MEMA = 2-methoxyethyl methacrylate,
DEAEA = diethylamino ethyl acrylate,
MEA = 2-methoxyethyl acrylate,
ThEA = thymine ethyl acrylate,
ThAcMA = thymine acetoxyethyl methacrylate, and
PEGA = Poly(ethylene glycol) methyl ether acrylate,
Mn ~480.

Suitably m may be between 1 and 50, suitably 2 and 50.
Alternative polymers can comprise monomer compositions comprising

TABLE 2

| Polymer | MEMA (%) | DEAEA (%) | MEA %) | ThEA (%) | ThAcMA (%) |
|---|---|---|---|---|---|
| A | 26 | 25 | 48 | — | — |
| B | 22 | 36 | 34 | 7 | — |
| C | 11 | 46 | 35 | — | 8 |
| D | 18 | 34.5 | 43 | 4.5 | — |
| E | 22 | 30.5 | 30.5 | 17 | — |
| F | 18 | 35 | 41 | — | 6 |
| G | 27 | 36 | 23 | — | 14 |

Wherein
MEMA = 2-methoxyethyl methacrylate
DEAEA = diethylaminoethyl acrylate
MEA = 2- methoxyethyl acrylate
PEGA = poly(ethylene glycol) methyl ether acrylate
ThEA = thymine ethyl acrylate
ThAcMA = thymine acetoxyethyl methacrylate Suitably the polymer may have a molecular weight in the range 1000-500,000 Da. Suitably the polymer may have a molecular weight of at least 10,000 Da, at least 20,000 Da, at least 30,000 Da, at least 40,000 Da, at least 50,000 Da at least 60,000 Da. Suitably the polymer may have a molecular weight in the range 20,000 to 60,000 Da, suitably 30,000 to 60,000 Da.

Without wishing to be bound by theory, it is considered the nucleic acid reversibly binds to the polymer through a combination of electrostatic and H-bonding interactions under physiological conditions. By selective elution conditions the nucleic acid is eluted from the polymer and recovered with high-efficiency.

Suitably the sample may comprise at least one of a biological fluid, cell suspension, or tissue sample. Suitably the isolation and purification may be undertaken using a sample from a complex medium, such as blood or serum. Suitably the sample comprises blood or plasma. Suitably the nucleic acid may be cfDNA. In embodiments, for any of the above methods, the cfDNA can comprise single-stranded DNA, single-stranded RNA, double-stranded DNA, or double-stranded RNA or mixtures therein.

Suitably the method provides for isolation of cell free DNA (cfDNA) from a blood sample. Also presented are methods for preparing the isolated cfDNA for DNA amplification. Suitably the sample may be provided by an aqueous solution, which is a diluted or substantially undiluted blood sample from a higher eukaryotic organism. Suitably the method comprises adding to the aqueous solution a polymer of the invention, binding cfDNA to the polymer, separating the cfDNA from the aqueous solution without the use of centrifugation or pre-filtration; optionally washing the cfDNA one or more times with a wash solution such that at least most of the cfDNA remains bound to the polymer, and optionally releasing the cfDNA therefrom.

Suitably the method provides for processing a sample comprising cfDNA. The method can comprise immobilising the sample in a polymer matrix, in an aqueous environment. The method can comprise removing non-cfDNA from the polymer while the cfDNA remains on polymer. The method can comprise separating the cfDNA from the polymer.

In embodiments, for any of the above methods, a single stranded nucleic acid, in particular cfDNA can comprise at least 50 bases, at least 100 bases, at least 160 bases, at least 200 bases, at least 500 bases. Suitably the polymer may also bind nucleic acid, in particular cfDNA comprising at least 1 kilobases (kb), at least 10 kb, at least 25 kb, at least 50 kb, at least 100 kb, at least 150 kb, at least 200 kb, for example, at least about 200 kb, 250 kb, 300 kb, 350 kb, 400 kb, 450 kb, 500 kb, 550 kb, 600 kb, 650 kb, 700 kb, 750 kb 850 kb, 950 kb or 1000 kb, including ranges between any two of the listed values. Advantageously, smaller fragments (from about 25 to 300 bases) suitably about 160 bases are bound by the polymer for use in any of the above methods.

In embodiments, for any of the above methods, a double stranded nucleic acid, in particular cfDNA can comprises at at least 50 bp, at least 100 bp, at least 160 bp, at least 200 bp, at least 500 bp. Suitably the polymer may also bind nucleic acid, in particular cfDNA comprising at least 1 kilobasepairs (kbp), at least 10 kbp, at least 25 kbp, at least 50 kbp, at least 100 kbp, at least 150 kbp, at least 200 kbp, for example, at least about 200 kbp, 250 kbp, 300 kbp, 350 kbp, 400 kbp, 450 kbp, 500 kbp, 550 kbp, 600 kbp, 650 kbp, 700 kbp, 750 kbp 850 kbp, 950 kbp or 1000 kbp, including ranges between any two of the listed values. Advantageously, smaller fragments (from about 25 to 300 bp) suitably about 160 bp are bound by the polymer for use in any of the above methods.

Suitably the polymer may be used to stabilise immobilised/isolated nucleic acid. This may advantageously allow isolated nucleic acid to be shipped or transported or stored whilst minimising degradation. Degradation may be minimised for at least 2 days, at least 4 days, at least 5 days, at least 7 days.

Suitably the method may comprise detecting the binding of nucleic acid to the polymer. Suitably the method may comprise immobilising the nucleic acid on the polymer to allow a reaction to be undertaken on the nucleic acid, for example to label the nucleic acid, sequence the nucleic acid, amplify the nucleic acid, recovering the nucleic acid or the like.

Suitably the method may comprise separating the nucleic acid, in particular cfDNA from the polymer. The method may comprise characterising the nucleic acid. In embodiments, characterisation can comprise determining a concentration, a quality metric, a physical map, a sequence content, an epigenetic information, a SNP, a haplotype, an RFLP, a sizing, a copy number variants, or any combination of these.

Often the volume of blood that can be drawn in both a clinical and research context is limited. It is highly beneficial to remove the cfDNA from the blood without requiring large volumes of blood being permanently removed from the circulation. The apheresis approach has the advantage of harvesting large quantities of cfDNA from large volumes of blood and then returning all other blood components back to a patient's circulation.

Suitably, the polymer of the invention may be haemocompatible during apheresis. Suitably, the polymer of the invention used during apheresis may cause minimal coagulation.

According to a second aspect of the present invention there is provided a nucleobase containing polymer wherein the nucleobase containing polymer comprises a polymer backbone and at least a proportion of nucleobase side chains selected from one or more of the following: adenine (A), cytosine (C), guanine (G), thymine (T), uracil (U) or a derivative thereof or combinations thereof. Suitably side chains of the polymer backbone may also comprise one or more of the following: amines, amides, alcohols, carboxylic acids, alkanes, alkenes, alkynes, esters, ethers, epoxies, sulfonyl hydrides, sulfonyls, thiols, heterocycles, homocycles, aromatic cycles, anti-aromatic cycles, or derivatives thereof, or combinations thereof. Suitably the proportion of side chains of the polymer comprising a nucleobase may be at least 5%, at least 10%, at least 15%, at least 20%. Suitably, nucleobase based side chains may be ordered, randomised or semi-randomised.

Suitably a nucleobase may be as described above.

Suitably the polymer may contain positively charged moieties at physiological pH.

Suitably the nucleobase based side chains may comprise a fused-ring skeletal structure derived of purine or pyrimidine or a combination of these. Suitably the nucleobase based side chains comprise a nucleobase selected from adenine (A), cytosine (C), guanine (G), thymine (T), uracil (U) or a derivative thereof and combinations thereof. For example, a suitable nucleobase derivative may comprise hypoxanthine, xanthine, 7-methylguanine, 5,6, dihydrouracil, 5-methyl cytosine, 5-hydroxymethylcytosine, 3-Nitropyrrole, 5-Nitroindole, 2,6-diaminopurine, pyrene or a combination thereof.

Suitably the nucleobase based side chains may contain cytosine or thymine or a combination of cytosine and thymine. Suitably a polymer for use in the method may be synthesised from monomers comprising either acrylates and/or methacrylates using acrylate polymerisation chemistry. A number of methods of acrylate polymerisation chemistry exist. Suitably, the synthesis of the nucleobase containing ter, tetra, or pentapolymers or such like may be by RAFT polymerisation.

Suitably the nucleobase-based monomers may be either or both thymine ethylacrylate or thymine acetoxylethyl methacrylate.

Suitably, the polymer backbone may be synthesised from monomers based on 2-methoxyethyl acrylate/methacrylate, diethylamino ethylacrylate, 2-methoxyethyl acrylate, 2-methoxyethyl methacrylate, diethylamino ethylacrylate, diethylamino ethyl methacrylate, hydroxyethyl acrylate, hydroxyethyl methacrylate, methyl methacrylate, methyl acrylate, styrene, methyl styrene, glycidyl acrylate, glycidyl methacrylate, N-vinylacetamide, 2-methyl-2-nitropropyl methacrylate, acrylic acid, methacrylic acid, 2-[[(butylamino)carbonyl]oxy] ethylacrylate, dimethylamino ethyl acrylate, dimethylamino ethyl methacrylate, mono-2-(acryloyloxy)ethyl succinate, poly(ethylene glycol) methyl ether acrylate/methacrylate or combinations thereof. Suitably monomers of different molecular weights may be provided to form the polymer. Suitably the polymers may be composed of at least two types of monomers. Suitably these different monomers may be of different molecular weights. Suitably monomers of poly(ethylene glycol) methyl ether acrylate/methacrylate may be provided with different or a range of molecular weights. Suitably the polymers may be terpolymers or tetrapolymers or pentapolymers. Suitably the polymer backbone may be synthesised using at least 10% of diethylaminoethylacrylate.

Suitably the polymer may be synthesised from acrylate/methacrylate-based monomers. Advantageously polymers formed from acrylate/methacrylate-based monomers with nucleobase side chains, and side chains selected from MEA, MEMA and PEGA side chains have been determined to resist biofouling. Suitably the monomers may comprise a methacryloyl-type monomer.

Suitably the polymer may be synthesised comprising or consisting at least one monomer selected from about 0-50% 2-methoxyethyl acrylate, about 0-50% 2-methoxyethyl methacrylate, about 0-50% diethylamino ethyl acrylate, in combination with at least one monomer selected from about 0-50% thymine ethyl acrylate, and about 0-50% thymine acetoxylethyl methacrylate. Suitably the polymers may provide the monomers in a randomised or semi-randomised sequence.

Suitably the polymer may be synthesised comprising or consisting at least one monomer selected from about 0-50% 2-methoxyethyl acrylate, about 0-50% 2-methoxyethyl methacrylate, about 0-50% diethylamino ethyl acrylate, about 0-50% poly(ethylene glycol) methyl ether acrylate in combination with at least one monomer selected from about 0-50% thymine ethyl acrylate, and about 0-50% thymine acetoxylethyl methacrylate. Suitably the polymers may provide the monomers in a randomised or semi-randomised sequence.

Suitably the polymer may be synthesised comprising or consisting at least one monomer selected from about 10-50% 2-methoxyethyl acrylate, about 0-40% 2-methoxyethyl methacrylate, about 1-40% diethylamino ethyl acrylate, in combination with at least one monomer selected from about 0-25% thymine ethyl acrylate, and about 0-25% thymine acetoxylethyl methacrylate. Suitably the polymers may comprise a randomised or semi-randomised sequence of such monomers.

Suitably the polymer may be synthesised comprising or consisting at least one monomer selected from about 10-50% 2-methoxyethyl acrylate, about 0-40% 2-methoxyethyl methacrylate, about 1-40% diethylamino ethyl acrylate, about 0-25% poly(ethylene glycol) methyl ether acrylate, in combination with at least one monomer selected from about 0-25% thymine ethyl acrylate, and about 0-25% thymine acetoxylethyl methacrylate. Suitably the polymers may comprise a randomised or semi-randomised sequence of such monomers.

Suitably the polymer may be synthesised comprising or consisting at least one monomer selected from about 30-50% 2-methoxyethyl acrylate, about 10-30% 2-methoxyethyl methacrylate, about 25-45% diethylamino ethyl acrylate, in combination with at least one monomer selected from about 0-15% thymine ethyl acrylate, and about 0-15% thymine acetoxylethyl methacrylate. Suitably the polymers may comprise a randomised or semi-randomised sequence of such monomers.

Suitably the polymer may be synthesised comprising or consisting at least one monomer selected from about 30-50% 2-methoxyethyl acrylate, about 20-40% 2-methoxyethyl methacrylate, about 20-40% diethylamino ethyl acrylate, about 0-15% poly(ethylene glycol) methyl ether acrylate, in combination with at least one monomer from about 0-15% thymine ethyl acrylate, and about 0-15% thymine acetoxylethyl methacrylate. Suitably the polymers may comprise a randomised or semi-randomised sequence of such monomers.

Suitable the polymer may be synthesised comprising or consisting monomers of about 18% 2-methoxyethyl methacrylate; about 35% diethylamino ethyl acrylate, about 42% 2-methoxyethyl acrylate, and about 5% thymine ethyl acrylate or thymine acetoxyethyl methacrylate.

Suitable the polymer may be synthesised comprising or consisting monomers of about 39% 2-methoxyethyl methacrylate; about 30% diethylamino ethyl acrylate, about 30% 2-methoxyethyl acrylate, about 1% poly(ethylene glycol) methyl ether acrylate, and about 1% thymine ethyl acrylate or thymine acetoxyethyl methacrylate.

Suitably a polymer may comprise or consist:

2-methoxyethyl methacrylate—47%

Diethylamino ethyl acrylate—15%

2-methoxyethyl acrylate—36%

Thymine ethyl acrylate—1%

Poly(ethylene glycol) methyl ether acrylate Mn 480-1%.

In embodiments the polymer (such as ms26, ms28 or msX) may be provided by:

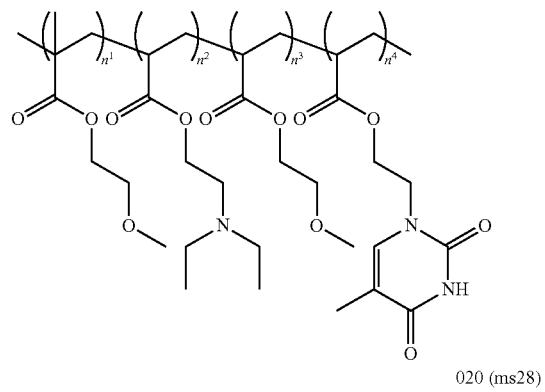

010 (ms26)

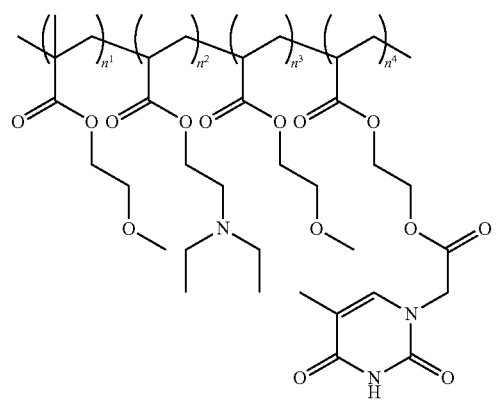

020 (ms28)

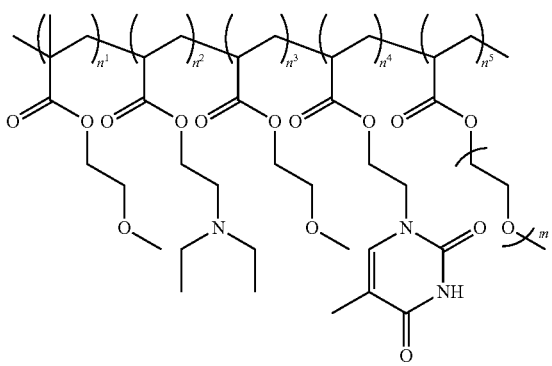

030 (msX or msY)

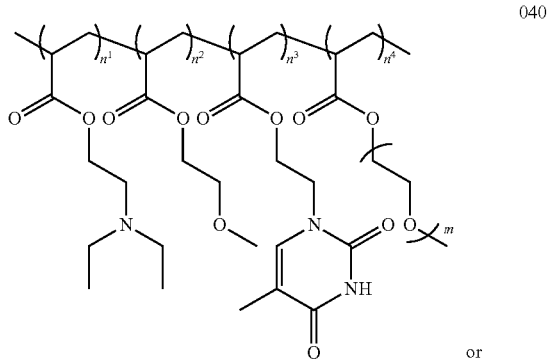

040

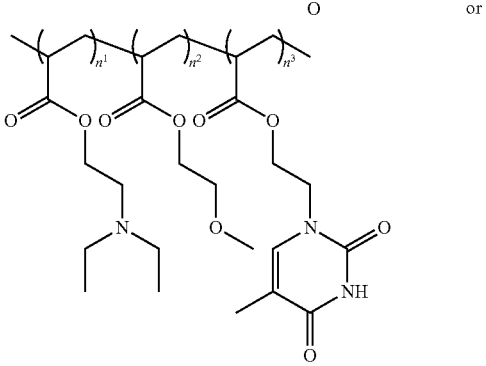

or

Suitably the monomers used to synthesise such polymers are incorporated randomly. Those of skill in the art will appreciate that $n^1$, $n^2$, $n^3$, $n^4$, or $n^5$ may be suitably selected to provide a % composition as discussed herein. Suitably the monomers used to synthesise such polymers are incorporated randomly.

Suitably a polymer may be provided having a proportion of monomers as set out in Table 1.

TABLE 1

| | MEMA (%) | DEAEA (%) | MEA (%) | ThEA (%) | ThAcMA (%) | PEGA (%) |
|---|---|---|---|---|---|---|
| Ms13 | 39 | 32 | 29 | — | — | — |
| Ms22 | 38 | 27 | 29 | 6 | — | — |
| Ms23 | 37 | 26 | 28 | — | 9 | — |
| Ms26 | 42 | 25 | 32 | 1 | — | — |
| Ms27 | 38 | 26 | 28 | 8 | — | — |
| Ms28 | 39 | 28 | 29 | — | 4 | — |
| Ms29 | 33 | 28 | 25 | — | 14 | — |
| MsY | 39 | 30 | 29 | 1 | — | 1 |
| MsX | 47 | 15 | 36 | 1 | — | 1 |

Those of skill in the art will appreciate that $n^1$, $n^2$, $n^3$, $n^4$, or $n^5$ may be suitably selected to provide a % composition as discussed herein. These are based on H-NMR data. The percentages refer to the integration/proportion of signal from each of the monomers as part of the polymer signal as a whole.

Alternative polymers can comprise monomer compositions comprising

TABLE 2

| Polymer | MEMA (%) | DEAEA (%) | MEA %) | ThEA (%) | ThAcMA (%) |
|---|---|---|---|---|---|
| A | 26 | 25 | 48 | — | — |
| B | 22 | 36 | 34 | 7 | — |
| C | 11 | 46 | 35 | — | 8 |
| D | 18 | 34.5 | 43 | 4.5 | — |
| E | 22 | 30.5 | 30.5 | 17 | — |
| F | 18 | 35 | 41 | — | 6 |
| G | 27 | 36 | 23 | — | 14 |

Wherein
MEMA = 2-methoxyethyl methacrylate
DEAEA = diethylaminoethyl acrylate
MEA = 2- methoxyethyl acrylate
PEGA = poly(ethylene glycol) methyl ether acrylate
ThEA = thymine ethyl acrylate
ThAcMA = thymine acetoxyethyl methacrylate Suitably the polymer may have a molecular size in the range 1000-500,000 Da. Suitably the polymer may have a molecular weight of at least 10,000 Da, at least 20,000 Da, at least 30,000 Da, at least 40,000 Da, at least 50,000 Da at least 60,000 Da. Suitably the polymer may have a molecular weight in the range 20,000 to 60,000 Da, suitably 30,000 to 60,000 Da.

Suitably the polymers may be provided on a substrate. Suitably, the substrate may, be formed of a polymer of the invention or may be coated by a polymer of the invention, for example coated onto a mesh, sponge, or filter that permits aqueous solutions (whole blood) to pass through yet contains a surface onto which nucleic acid, suitably cfDNA, can bind.

The substrate may incorporate material that exhibits permanent magnetic behaviour. The substrate may be composed of material that exhibits magnetic behaviour only when subjected to a magnetic field.

Identification of disease states can involve purification and optionally identification or quantification of polynucleotides of cfDNA. Suitably the method may comprise labelling polynucleotides of cfDNA for example to identify or quantify the cfDNA. Suitably sequencing of the nucleic acid, in particular cfDNA can be undertaken. Sequencing may be for example via Next Generation Sequencing. Suitably the nucleic acid may be used in PCR methods. Suitably the method may provide for analysis of the nucleic acid.

Suitably the nucleic acid, in particular cfDNA may be purified from the polymer without any labelling or characterization. The nucleic acid can then be used for any of a variety of downstream applications. It is contemplated that using methods as described herein, nucleic acid can be obtained from a complex starting material (for example blood), to provide isolated or purified nucleic acid, in particular cfDNA.

Suitably the nucleic acid, in particular cfDNA may be further analysed or utilised, for example by next generation sequencing or via PCR. A fluorophore, a quantum dot, a dendrimer, a nanowire, a bead, a hapten, a streptavidin, an avidin, a neutravidin, a biotin, and a reactive group a peptide, a protein, a magnetic bead, a radiolabel, or a non-optical label may be applied to the immobilised nucleic acid. In some embodiments, a label can be a fluorophore or a quantum dot.

Suitably, the nucleic acid, in particular cfDNA may be immobilized in or on a porous matrix, wherein the matrix is formed of the polymer or coated with or has the polymer applied thereto. In some embodiments, the porous matrix has a high surface area relative to its volume such as provided by a sponge or mesh. A high surface area can facilitate removal of non-nucleic acid molecules and other manipulations while the nucleic acid remains immobilized in or on the porous matrix. In some embodiments, the nucleic acid can be labelled, quantified, identified or stored while immobilized in or on the porous matrix or substrate. In some embodiments, the nucleic acid is removed from the matrix or substrate and then quantified, identified, further characterised or stored. Suitably a porous matrix can comprise pores to permit the movement of molecules such as non-nucleic acid molecules (e.g. molecules being removed from a sample) in, out, and within the matrix. Suitably the pore size may be about 100 μm to about 1000 μm.

Suitably the substrate comprising the polymer may be rigid. Suitably, the substrate comprising the polymer may be flexible. The substrate may comprise a surface of a slide, a container or a sheet. Suitably, the substrate may comprise a mesh or sponge. A sponge is particular advantageous to be formed by or covered with the polymer as it allows a high surface area for the nucleic acid to bind.

Advantageously the substrate comprising the polymer may have a high surface area, for example as provided by a sponge like material. Suitably the substrate may be provided by beads. The term "beads" includes but is not limited to particles that are spherical or irregular in nature and of size ranging from 0.1 micron to 10 micron in diameter.

In some embodiments, the polymer can be coated onto a mesh or structure comprising a plurality of openings, for example a sponge or sponge like structure having a diameter of about 100 μm to about 1000 mm.

In some embodiments, for any of the above methods, the substrate can comprise a loose or tight mesh or sponge, thereby allowing the polymer to be provided between or on one or more surfaces or fibres of the mesh or sponge, thereby immobilising the cfDNA which is bound by the polymer in a matrix.

Suitably, the polymer coated matrix may be provided on or as a substrate within a fluidic device. Suitably the fluidic device can be a flow cell for use in an apheresis device or extracorpeal device.

Suitably the polymer may form or be applied to a substrate, for example a mesh or sponge.

Accordingly, a third aspect of the invention provides a system wherein the system comprises a fluidic device and polymer of the second aspect of the invention. In embodiments the polymer can be provided inside or outside of a fluidic device. In embodiments, the fluidic device can be configured to control at least one of volumes, temperatures or fluidic movement of a sample, for example a blood sample, during the processing. In embodiments, a fluidic device can be configured to automatically perform the processing of the sample.

According to a fourth aspect of the present invention there is provided a fluidic device comprising a polymer of the invention. In embodiments the fluidic device can comprise a sample input path and a sample output path wherein the input path to output path extends over a polymer of the invention. The polymer may be provided as or on a sponge like structure to maximise contact of the sample with the polymer as it flows from the input path to the output path.

Accordingly, a fifth aspect of the present invention provides a kit comprising monomers for forming a polymer of the second aspect of the invention. Suitably the kit may comprise
a nucleobase-containing monomer,
a non-nucleobase-based monomer selected from 2-methoxyethyl acrylate/methacrylate, diethylamino ethylacrylate, 2-methoxyethyl acrylate, 2-methoxyethyl methacrylate, diethylamino ethylacrylate, diethylamino ethyl methacrylate, hydroxyethyl acrylate, hydroxyethyl methacrylate, methyl methacrylate, methyl acrylate, styrene, methyl styrene, glycidyl acrylate, glycidyl methacrylate, N-vinylacetaminde, 2-methyl-2-nitropropyl methacrylate, acrylic acid, methacrylic acid, 2-[[(butylamino)carbonyl]oxy] ethylacrylate, dimethylamino ethyl acrylate, dimethylamino ethyl methacrylate, mono-2-(acryloyloxy) ethyl succinate, poly(ethylene glycol) methyl ether acrylate/methacrylate or combinations thereof, optionally 2-methoxyethyl acrylate/methacrylate, diethylamino ethylacrylate, hydroxyethyl methacrylate, methyl methacrylate, 2-methoxyethyl methacrylate, styrene, glycidyl methacrylate, N-vinylacetaminde, 2-methyl-2-nitropropyl methacrylate, acrylic acid, methacrylic acid, 2-[[(butylamino)carbonyl]oxy] ethylacrylate, dimethylamino ethyl methacrylate, dimethylamino ethylacrylate, mono-2-(acryloyloxy)ethyl succinate, poly(ethylene glycol) methyl ether acrylate/methacrylate, terpolymers, tetrapolymers or pentapolymers or greater than five monomers linked to form a polymer, or a combination thereof.

Suitably, the nucleobase-containing monomers may be thymine ethylacrylate or thymine acetoxylethyl methacrylate. Suitably, the nucleobase-containing monomers may alternatively be nucleobases as known in the art, for example nucleobases as discussed herein. Suitably the kit may comprise monomers to form a polymer as described herein.

In embodiments, the monomers of the kit can comprise at least one of 2-methoxyethyl acrylate, 2-methoxyethyl methacrylate, diethylamino ethyl methylacrylate, diethylamino ethyl acrylate, and the nucleobase containing monomer can be selected from at least one of thymine ethyl acrylate, and thymine acetoxylethyl methacrylate.

In embodiments, the monomers of the kit can comprise at least one of 2-methoxyethyl acrylate, 2-methoxyethyl methacrylate, diethylamino ethyl methylacrylate, diethylamino ethyl acrylate, poly(ethylene glycol) methyl ether methacrylate, poly(ethylene glycol) methyl ether acrylate, and the nucleobase containing monomer can be selected from at least one of thymine ethyl acrylate, and thymine acetoxylethyl methacrylate.

Suitably the kit may provide at least one of the monomers in an amount selected from 0-50% 2-methoxyethyl acrylate, about 0-50% 2-methoxyethyl methacrylate, about 0-50% diethylamino ethyl methylacrylate, and at least one of about 0-50% thymine ethyl acrylate, and about 0-50% thymine acetoxylethyl methacrylate.

Suitably the kit may provide at least one of the monomers in an amount selected from 0-50% 2-methoxyethyl acrylate, about 0-50% 2-methoxyethyl methacrylate, about 0-50% diethylamino ethyl methylacrylate, 0-50% poly(ethylene glycol) methyl ether methacrylate, 0-50% poly(ethylene glycol) methyl ether acrylate and at least one of about 0-50% thymine ethyl acrylate, and about 0-50% thymine acetoxylethyl methacrylate.

Suitably the kit may provide at least one of the monomers in an amount selected from 0-15% 2-methoxyethyl acrylate, about 0-15% 2-methoxyethyl methacrylate, about 0-15% diethylamino ethyl methylacrylate, about 0-15% diethylamino ethyl acrylate, about 0-15% thymine ethyl acrylate, and about 0-15% thymine acetoxylethyl methacrylate.

Suitably the kit may provide at least one of the monomers in an amount selected from 0-15% 2-methoxyethyl acrylate, about 0-15% 2-methoxyethyl methacrylate, about 0-15% diethylamino ethyl methylacrylate, about 0-15% diethylamino ethyl acrylate, about 0-15% poly(ethylene glycol) methyl ether acrylate, about 0-15% thymine ethyl acrylate, and about 0-15% thymine acetoxylethyl methacrylate.

Suitably the kit may comprise a substrate, for example a mesh or sponge to which the synthesised polymer can be applied.

Suitably the kit may comprise a polymer of the invention and an organic solvent, for example THF, into which the polymer can be dissolved. Suitably the dissolved polymer and solvent composition may be provided to substrates to be coated with the polymer, for example a sponge or mesh.

Definitions

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of this disclosure, suitable methods and materials are described below. The term "comprises" means "includes." Additionally, the terms "comprising" and "comprised of" are intended to include embodiments encompassed by the terms "consisting essentially of" and "consisting of." Similarly, the term "consisting essentially of" is intended to include embodiments encompassed by the term "consisting of." The abbreviation, "e.g." is derived from the Latin exempli gratia, and is used herein to indicate a non-limiting example. Thus, the abbreviation "e.g." is synonymous with the term "for example."

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Aqueous sample: Any sample that is water-based and does not include alcohols or other water soluble organic solvents. In particular embodiments, an aqueous sample or solution contains a blood sample mixed into it at 10%, 20%, 30%, 40%, 50% or even greater concentration. In other particular embodiments, the aqueous sample is a 100% blood sample that has been minimally processed from the time of extraction from a subject.

Blood sample: Any blood sample drawn from a subject. As used herein, a blood sample can be a 100% whole blood sample. In other embodiments, a blood sample can be diluted in a suitable aqueous solution to 90%, 80%, 70%, 60%, 50%, 40%, 30%, 20%, and 10% of the starting sample concentration. A blood sample need not be whole blood, so long as a nucleic acid can be isolated from the nucleic acid containing portion, for example a cfDNA containing portion of the original whole blood. In particular examples, the blood sample is "substantially undiluted" such as those examples wherein the sample is collected in or transferred to a collection receptacle containing small quantities of a reagent such as heparin, required for maintenance of the sample in liquid state and/or preservation of the blood sample.

The process of cfDNA isolation or purification does not require 100% purity; however, the end-product of cfDNA purification is cfDNA that may be used in downstream applications such as cfDNA sequencing, PCR, and the like. In a particular embodiment, cfDNA purification involves binding cfDNA released and/or extracted from a cell to a polymer; washing away or otherwise removing other components of the sample that was with the cfDNA; and separating the isolated cfDNA with an elution buffer to separate the cfDNA from the support into a buffer solution in preparation for cfDNA amplification and/or identification, as for example, real-time PCR.

Preferred compositions, features and embodiments of each aspect of the invention are as for each of the other aspects mutatis mutandis unless context demands otherwise.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

Figure 2:
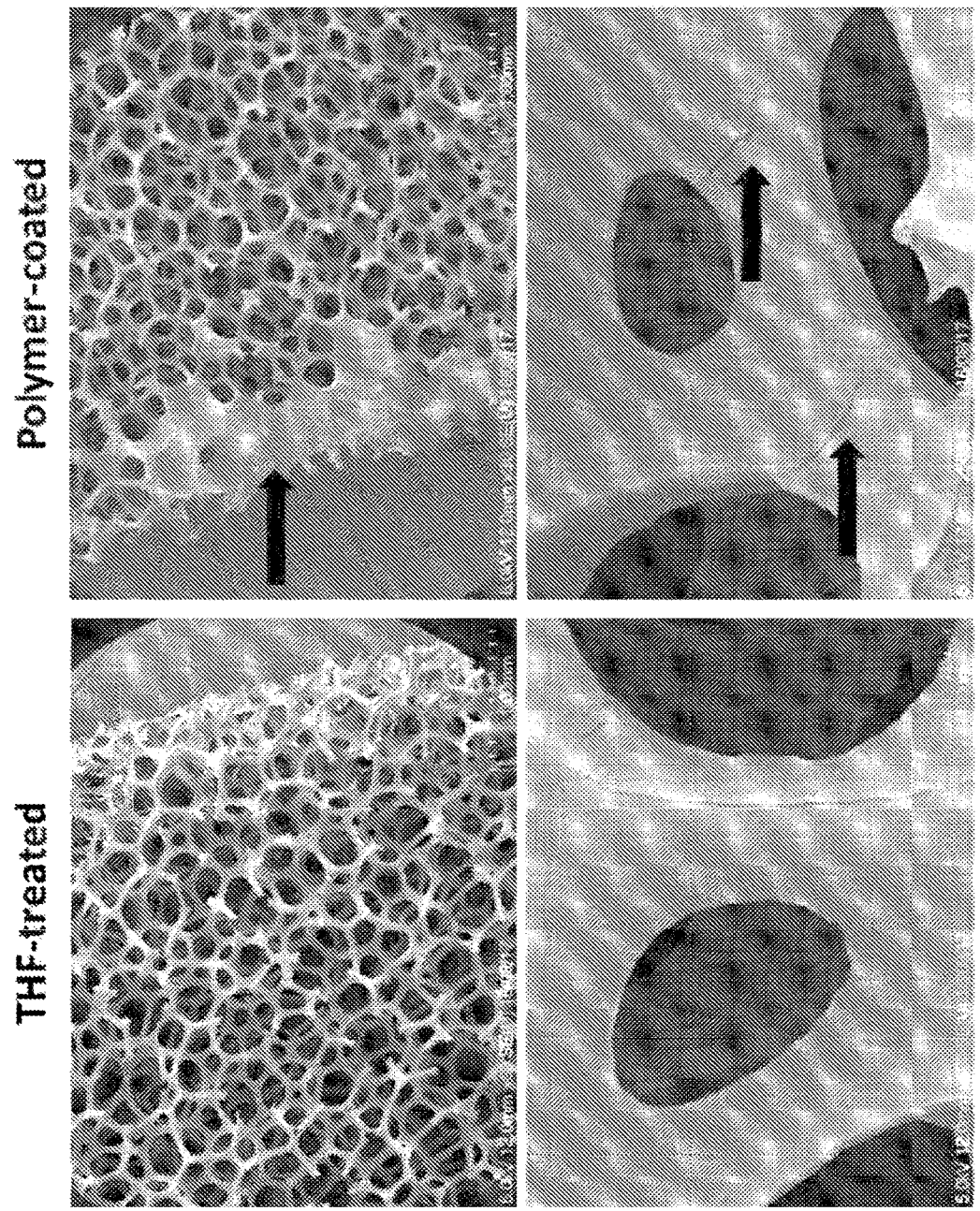
Figure 3:
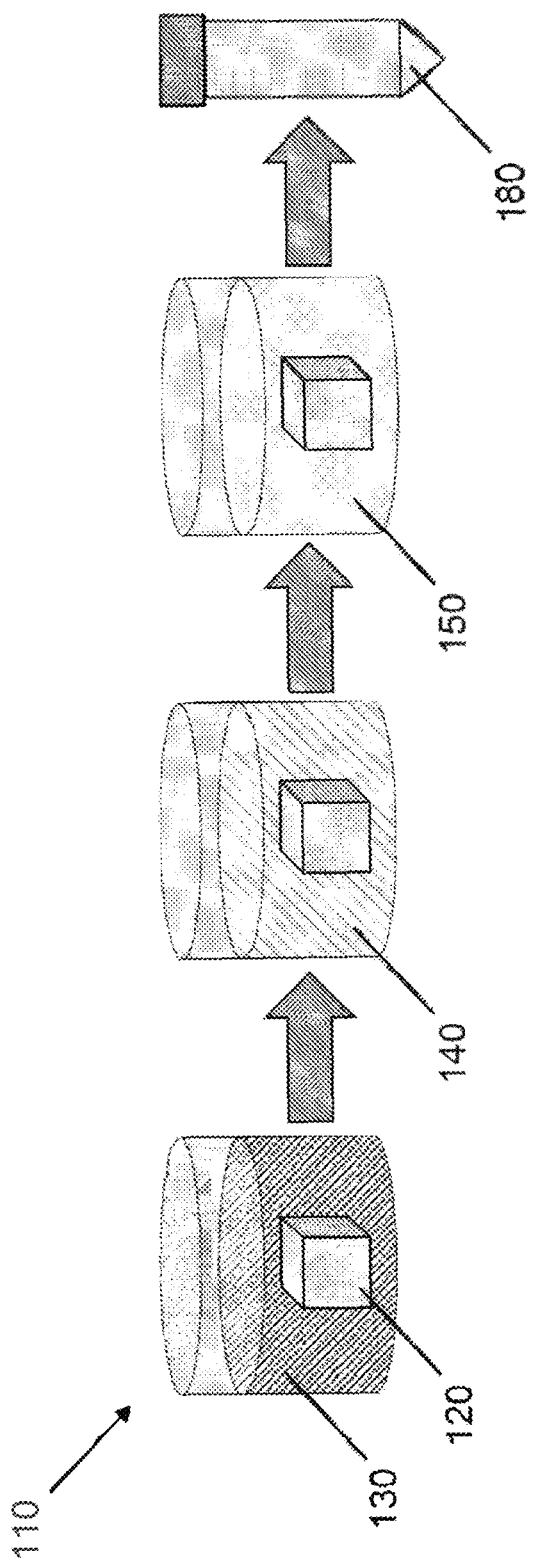
Figure 4:
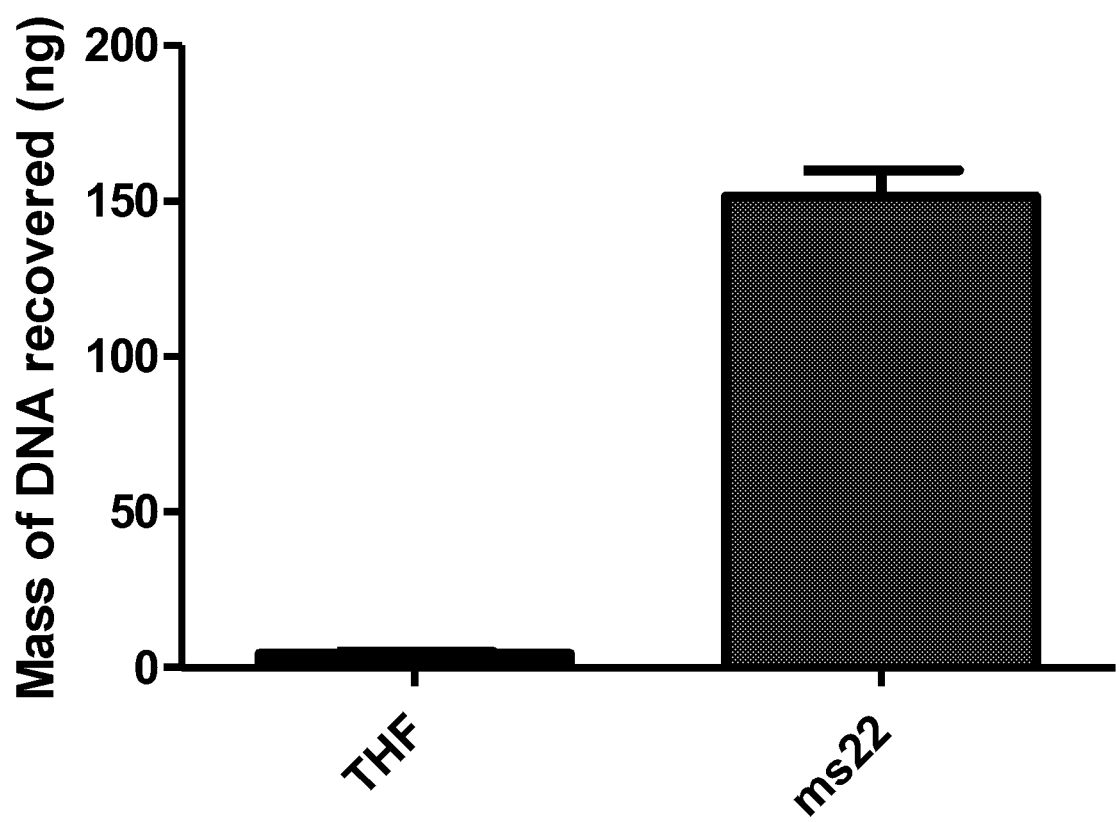
Figure 5:
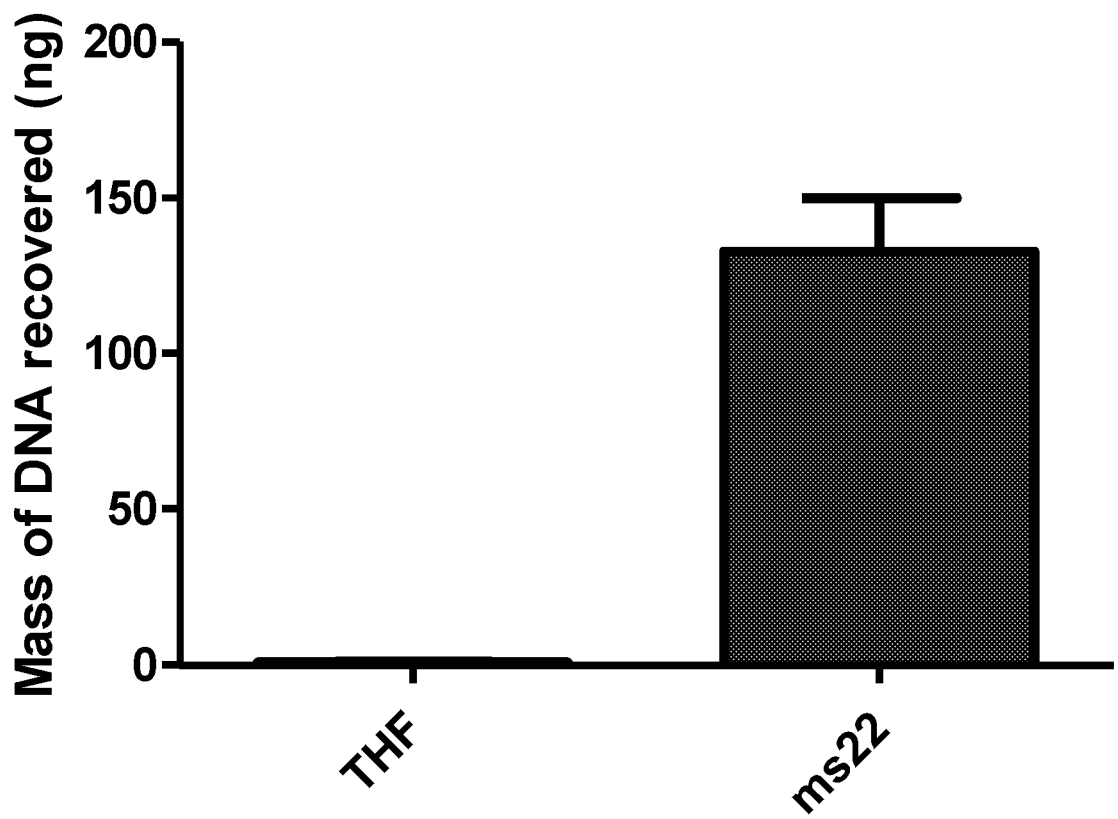
Figure 6:
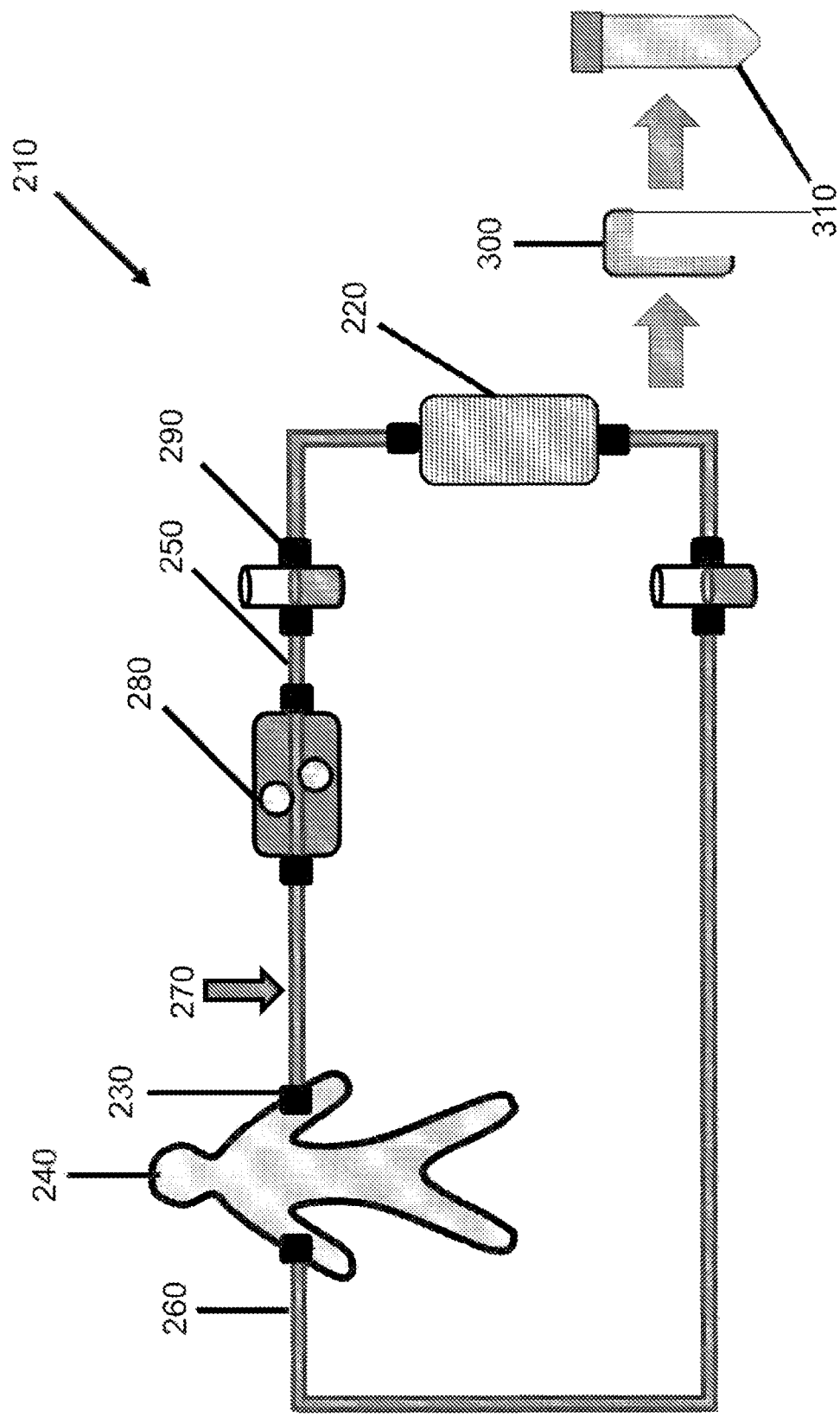
Figure 7:
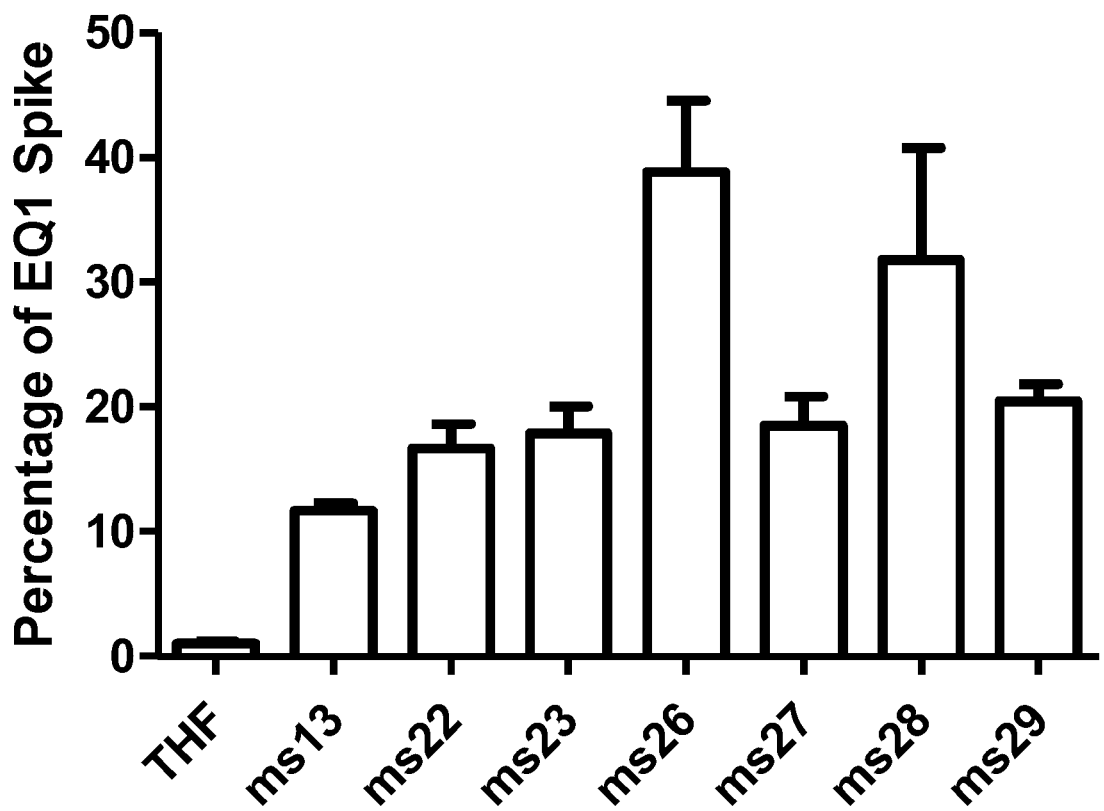
Figure 8:
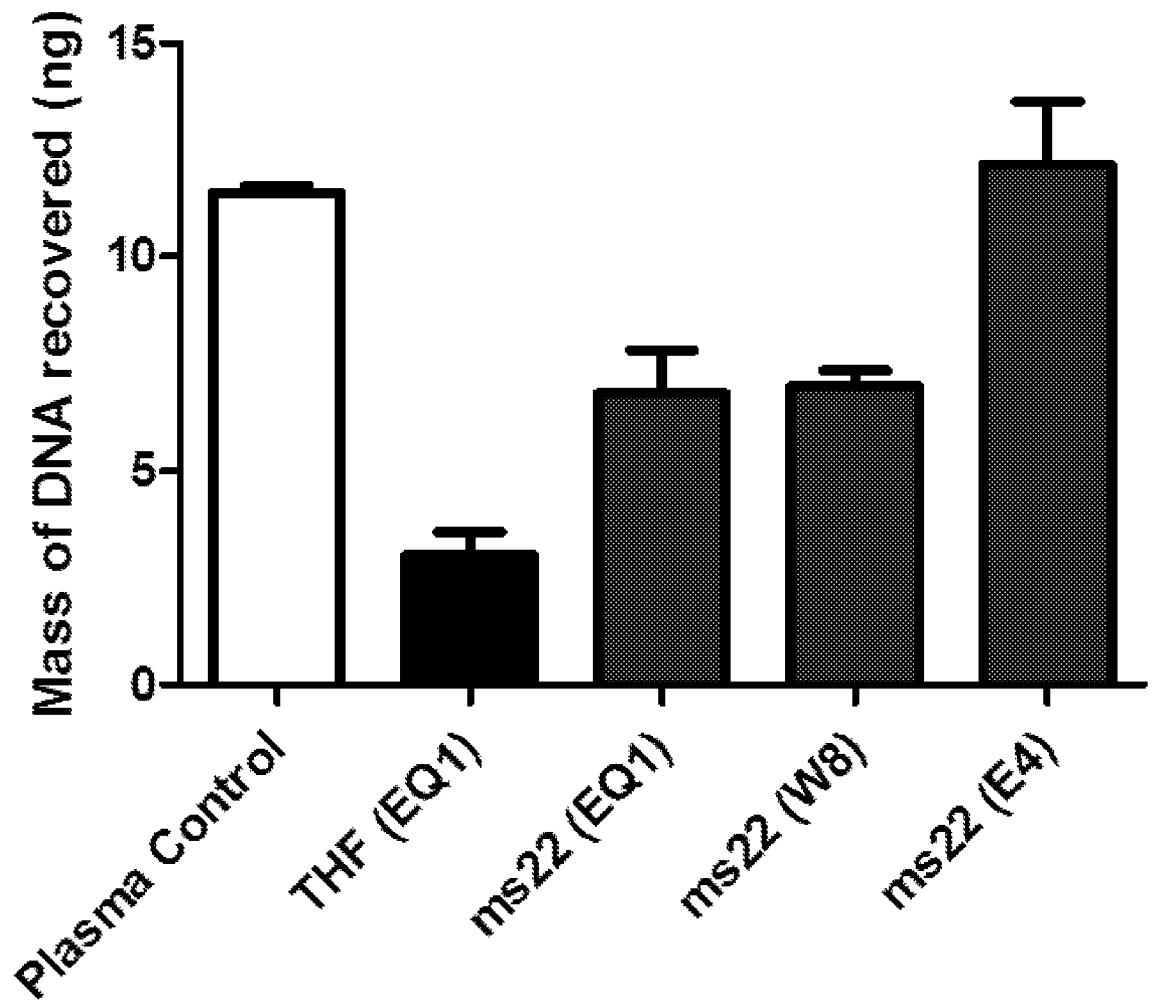

Embodiments of the present invention will now be described with reference to the accompanying figures, by way of example only, in which:

FIG. 1: illustrates the synthesis of nucleobase containing polymers comprising thymine derivatives;

FIG. 2: illustrates substrates provided with the nucleobase containing polymers in which the polymers are provided on support mesh or sponge substrates to provide high surface areas for nucleic acid binding, the arrows noting a coating on the substrate;

FIG. 3: provides an overview of cfDNA isolation using the methods of the invention;

FIG. 4: illustrates the recovery of DNA (150 ng) from aqueous solution using a 125 mm$^3$ polyurethane sponge coated with nucleobase containing polymer;

FIG. 5: illustrates the recovery of DNA (150 ng) from an aqueous solution blood mimic using a 125 mm$^3$ polyurethane sponge coated with nucleobase containing polymer following 30 minutes of cycling the blood mimic at 28 mL/min at 37° C.;

FIG. 6: illustrates an overview of an extracorporeal extraction cfDNA isolation using the methods of the invention for cfDNA sampling;

FIG. 7: illustrates the sequestering of radiolabelled cfDNA from whole blood using a range of nucleobase containing polymers;

FIG. 8: illustrates the elution of cfDNA after scavenging from whole blood. The elution buffers used were EQ1 buffer=0.1 M sodium acetate pH 5, 0.6 M NaCl, 0.15% Triton X-100; W8 buffer=0.1 M sodium acetate pH 5, 0.825 M NaCl and E4 buffer=0.1 M Tris-HCl pH 8.5, 1.25 M NaCl.

Figure 9:
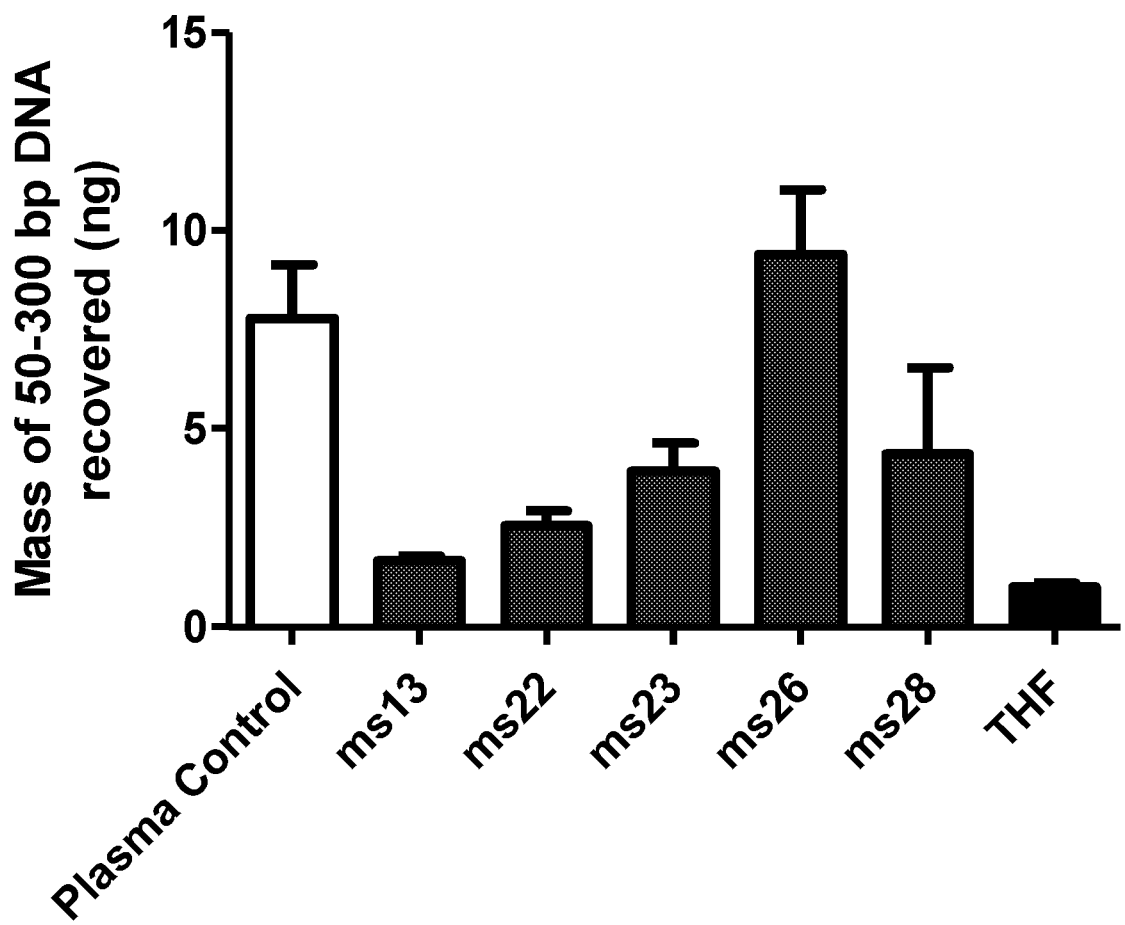

FIG. 9: illustrates polymers (MS13=30% diethylaminoethylacrylate, MS22-28=30% diethylaminoethylacrylate and thymine monomer) based on DNA recovery yields after incubation with whole blood (human) spiked with DNA (mouse mononucleosomal). DNA was quantified by HS Qubit™ and submitted for size analysis. Mouse mononucleosomal DNA (a model of cfDNA) was detected between 50-300 bp;

FIG. 10: provides details of polymer compositions; and

Figure 11:
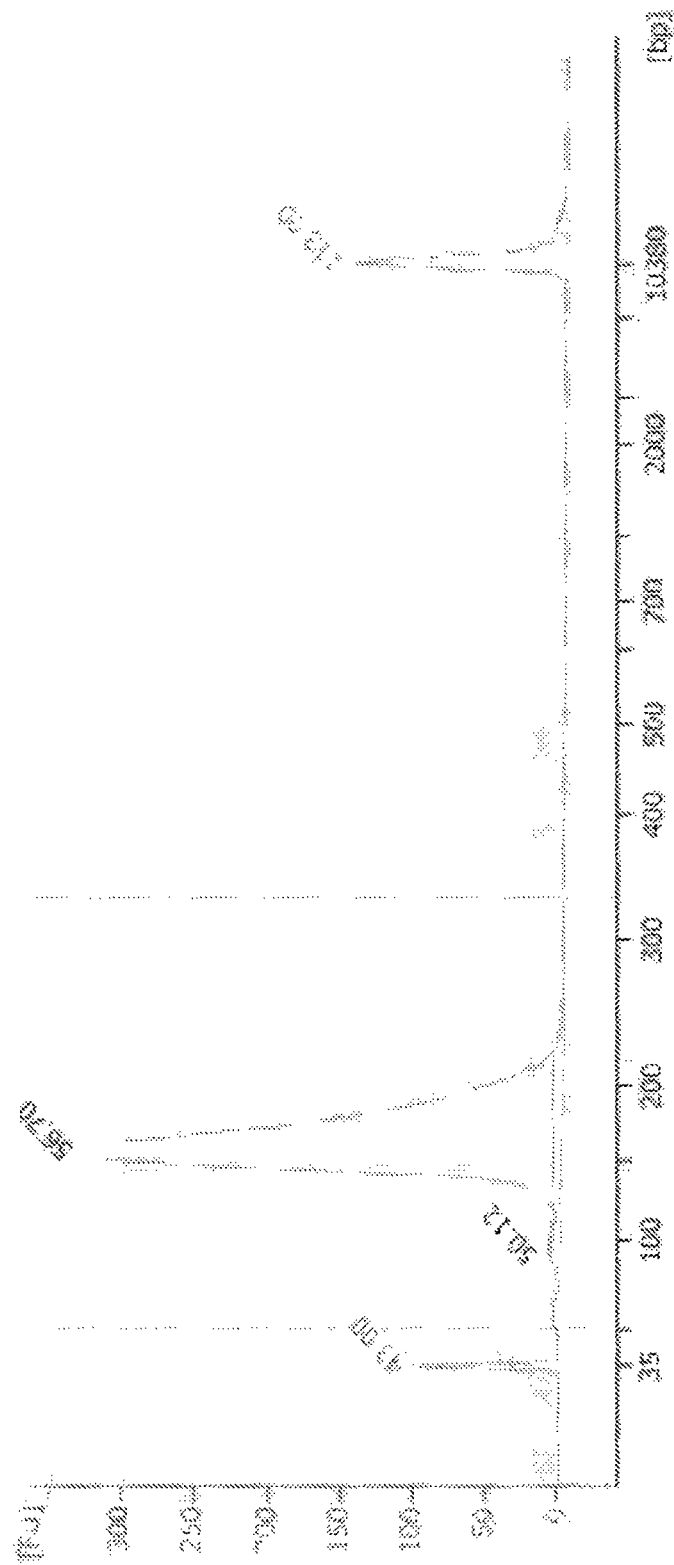
Figure 11:
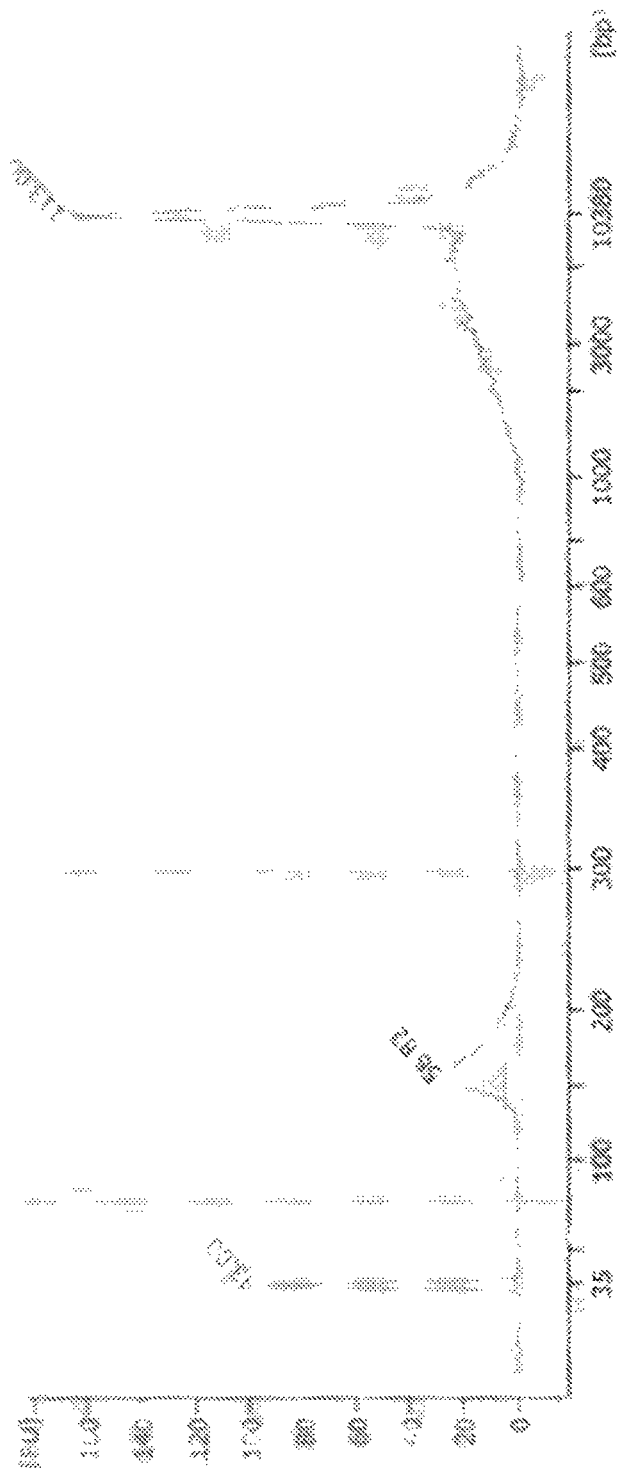
Figure 11C:
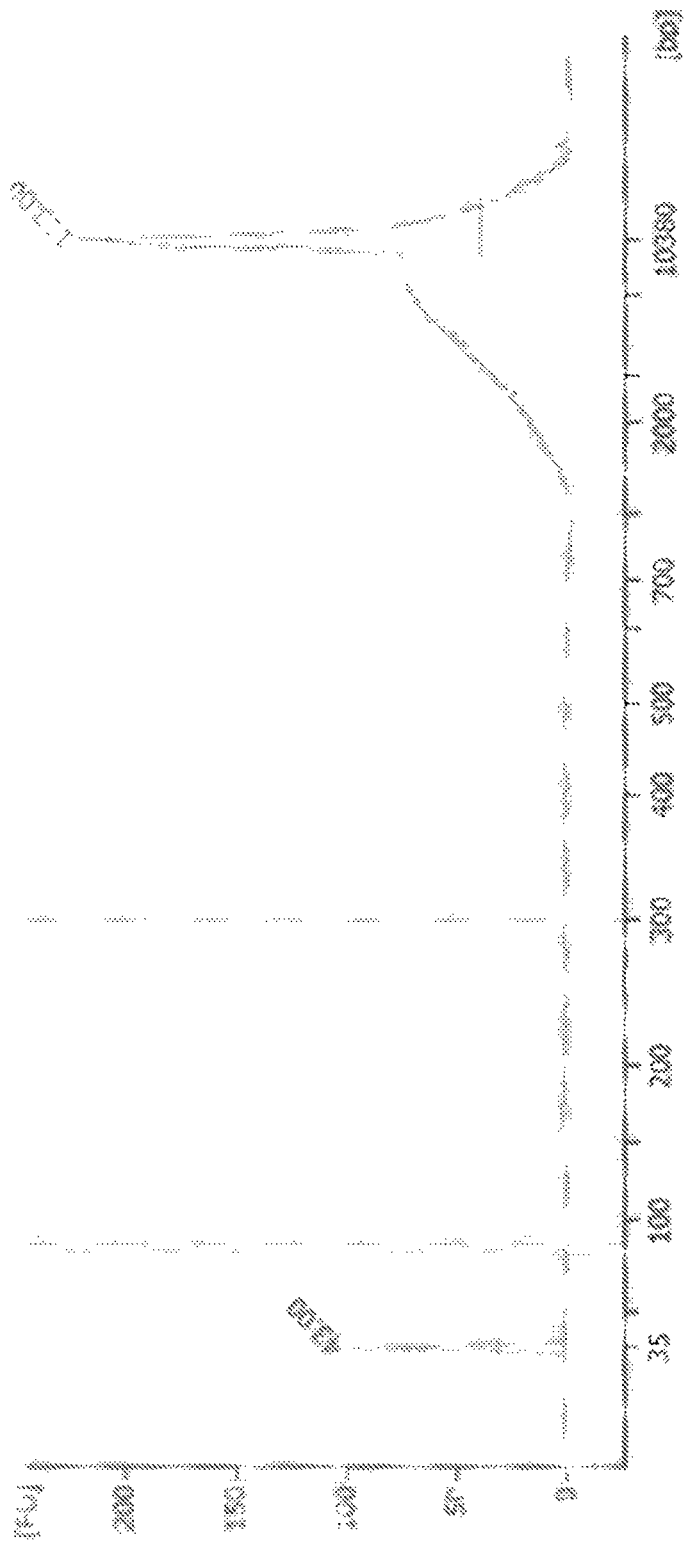

FIG. 11: illustrates Bioanalyzer traces (DNA fragment size analysis) and demonstrates successful recovery of small fragment DNA by the polymer-coated sponge but not by the sponge alone (A) Pure mononucleosomal DNA, (B) DNA recovered by polymer, and (C) DNA recovered by THF negative control.

FIG. 12: illustrates a number of polymers of the invention, where m=2-50.

FIG. 13: illustrates the haemocompatibility of a range of polymers of the invention. Polymer-coated sponges prepared using different concentrations of coating solutions were prepared, and a qualitative evaluation of coagulation was performed, where '+'=coagulation observable and '−'=no evidence of coagulation.

Figure 14:
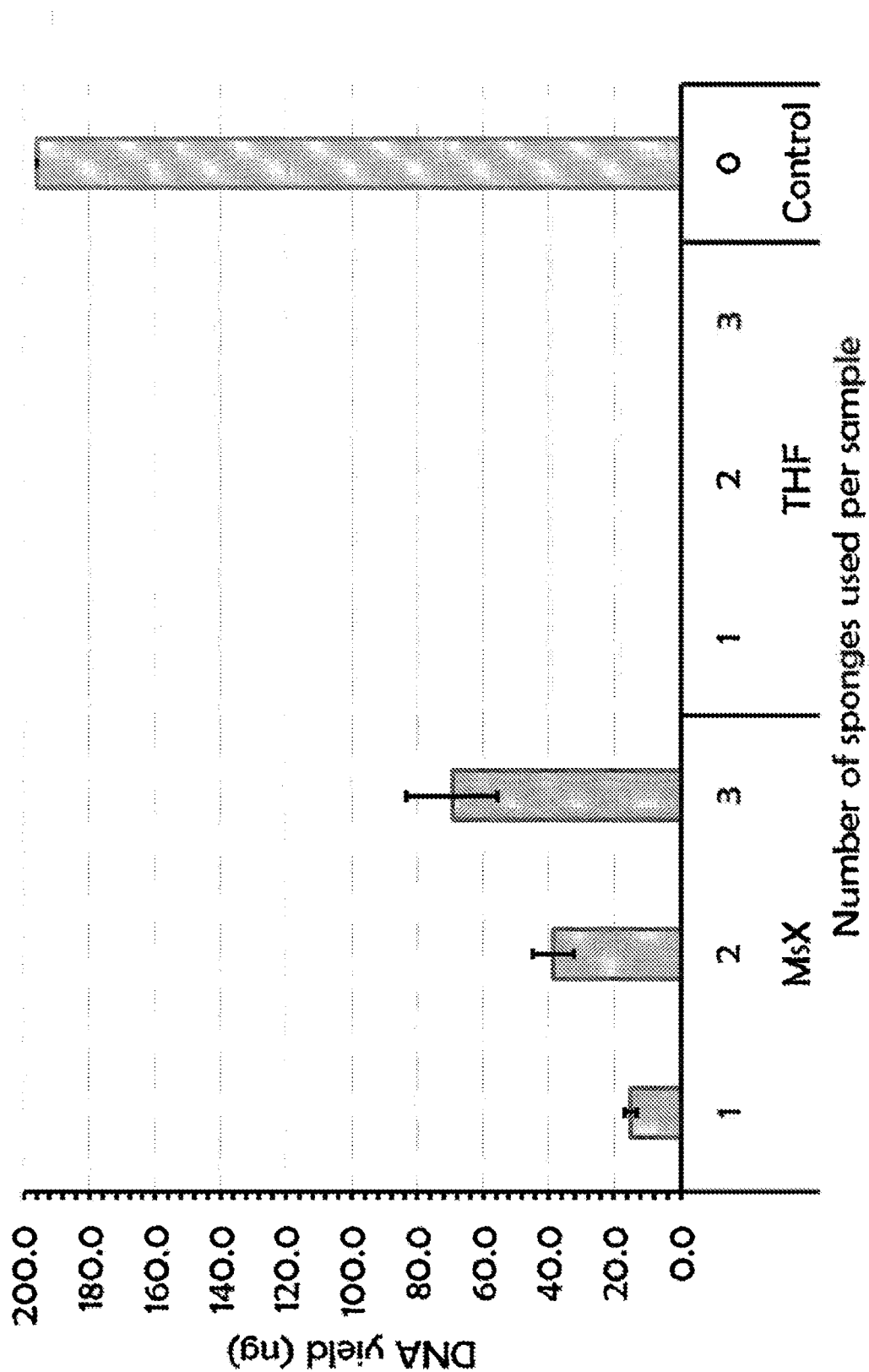

FIG. 14: illustrates DNA recovery from polymers of the invention (msX) compared with THF sponges using a flow-based setup. TE buffer spiked with 200 ng mononucleosomal DNA (160 bp) was incubated with either 1, 2, or 3×125 mm$^3$ sponges. Bound DNA was eluted and quantified by HS Qubit™. (n=3, error bars show standard deviation).

Figure 15:
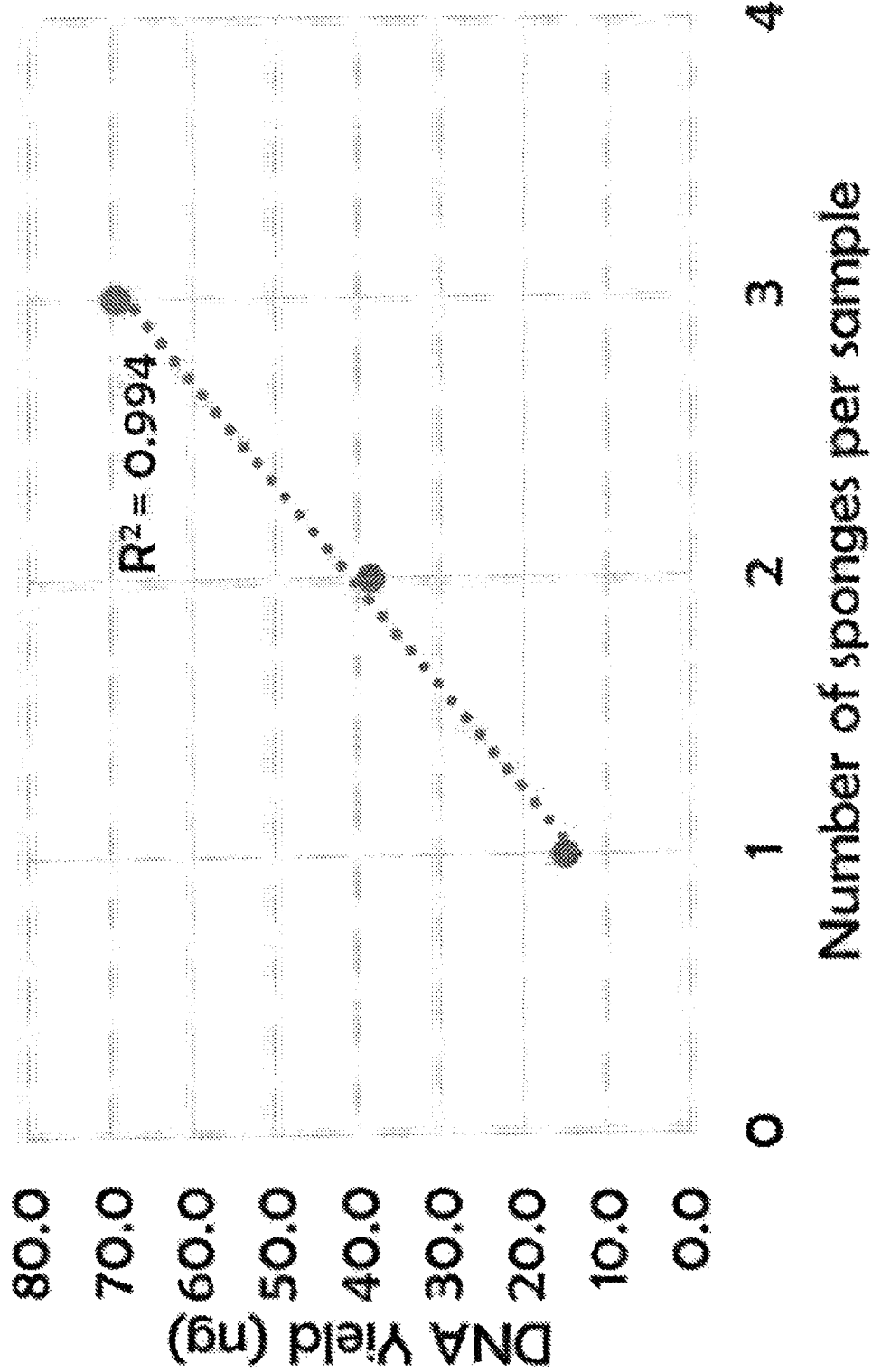

FIG. 15: illustrates the linear DNA binding capabilities of the msX-treated sponges of FIG. 14.

DETAILED DESCRIPTION

Example 1—Synthesis of the Polymers of the Invention

FIG. 1 summarises the synthesis of a polymer of the invention; whereby a polymerisation reaction of acrylate/methacrylate monomers results in a nucleobase containing polymer. Monomers were combined in the presence of a chain transfer agent (2-Cyano-2-propyl dodecyl trithiocarbonate) and initiator (2,2'-Azobis(2-methylpropionitrile)) at a typical ratio of 1000:5:1, or 1500:5:1, in DMSO. The reaction was degassed with $N_2$ before heating to 60° C. for up to 7 days.

The reaction was stopped by cooling with dry ice and acetone, and exposed to air. The polymer was purified by precipitation first into water, then three times by dissolving in THF and precipitated in hexane. The polymer was then dried of solvent in a vacuum oven (40° C.).

Example 2—Synthesis of Specific Polymers of the Invention

Polymers were typically synthesised on a 1 g scale. Monomers were passed through basic alumina columns to remove inhibitors. Purified monomers were combined with chain transfer agent (2-cyano-2-propyl dodecyl trithiocarbonate), and AIBN (5:1) in a microwave vial and dissolved in DMSO to a final reaction concentration of 5 M. Reactions were degassed with $N_2$ for 30 min. Polymerisations were stirred at 60° C. under $N_2$ for 48 h. Reactions were quenched by exposing to air and cooling with acetone: dry ice. Polymers were first precipitated into water, then dissolved and re-precipitated three times using THF and hexane, respectively. Polymers were then dried by vacuum oven (40° C.).

Proportions of monomers that were used in the synthesis of the polymers are provided in Table A

TABLE A

| | MEMA (%) | DEAEA (%) | MEA (%) | ThEA (%) | ThAcMA (%) | PEGA (%) |
|---|---|---|---|---|---|---|
| Ms13 | 40 | 30 | 30 | — | — | — |
| Ms22 | 38 | 28.5 | 28.5 | 5 | — | — |
| Ms23 | 38 | 28.5 | 28.5 | — | 5 | — |
| Ms26 | 39 | 30 | 30 | 1 | — | — |
| Ms27 | 36 | 27 | 27 | 10 | — | — |
| Ms28 | 39 | 30 | 30 | — | 1 | — |
| Ms29 | 36 | 27 | 27 | — | 10 | — |
| MsY | 38.5 | 30 | 29.5 | 1 | — | 1 |
| MsX | 51 | 10 | 37 | 1 | — | 1 | wherein
MEMA = 2-methoxyethyl methacrylate,
DEAEA = diethylamino ethyl acrylate,
MEA = 2-methoxyethyl acrylate,
ThEA = thymine ethyl acrylate,
ThAcMA = thymine acetoxyethyl methacrylate, and
PEGA = Poly(ethylene glycol) methyl ether acrylate,
Mn ~480

$^1$H-NMR was used to measure the composition of the respective polymers following wherein the results are provided in Table B. More specifically, NMR characterisation was undertaken using a process wherein 5 mg of dried polymer was dissolved in 600 μL DMSO-d6 and submitted for compositional analysis using $^1$H-NMR, recorded using a Bruker AVA-500 at 500 MHz and 298 K. The broad peak corresponding to 2H (3.80-4.30 ppm) on the carbon alpha to the carboxylate on polymer side chains was set to represent 100% of the monomers components. This peak is shared by all monomers incorporated in the polymer. Individual monomer components were identified in reference to pure monomer samples, integrated, and calculated as a proportion of all monomers components.

TABLE B

| | MEMA (%) | DEAEA (%) | MEA (%) | ThEA (%) | ThAcMA (%) | PEGA (%) |
|---|---|---|---|---|---|---|
| Ms13 | 39 | 32 | 29 | — | — | — |
| Ms22 | 38 | 27 | 29 | 6 | — | — |
| Ms23 | 37 | 26 | 28 | — | 9 | — |
| Ms26 | 42 | 25 | 32 | 1 | — | — |
| Ms27 | 38 | 26 | 28 | 8 | — | — |
| Ms28 | 39 | 28 | 29 | — | 4 | — |
| Ms29 | 33 | 28 | 25 | — | 14 | — |
| MsY | 39 | 30 | 29 | 1 | — | 1 |
| MsX | 47 | 15 | 36 | 1 | — | 1 | wherein
MEMA = 2-methoxyethyl methacrylate
DEAEA = diethylamino ethyl acrylate,
MEA = 2-methoxyethyl acrylate,
ThEA = thymine ethyl acrylate,
ThAcMA = thymine acetoxyethyl methacrylate, and
PEGA = Poly(ethylene glycol) methyl ether acrylate,
Mn ~480

Example 3—Coating of the Polymers onto a Substrate

A nucleobase containing polymer was dissolved in THF and coated onto a support substrate provided by a sponge. FIG. 2 demonstrates this as viewed by scanning electron microscopy (SEM). Topographic changes highlight that the polymer has formed a layer on the surfaces of the substrate.

Example 4—Use of a Nucleobase Containing Polymer to Isolate DNA

An embodiment of the process of isolating DNA from a solution 110 is shown in FIG. 3, wherein a substrate comprising a polymer as discussed herein 120 would be provided in a solution of substantially undiluted whole blood 130, which comprises cfDNA. The cfDNA in the blood would then bind to the polymer. A wash buffer 140 would then be used to remove residual material from the whole blood while retaining the cfDNA on the polymer. The wash buffer in this embodiment would comprise phosphate buffered saline (PBS). An elution buffer 150 would then be provided to elute the cfDNA from the polymer. In this embodiment the elution buffer was 100 mM Tris-HCl pH 8.5, 1250 mM NaCl (high salt buffer with a NaCl concentration >600 mM). The elution may then be purified or concentrated using conventional means to produce an isolated cfDNA sample which may then be characterised.

In the present example, a 125 $mm^3$ polyurethane sponge was used as a substrate onto which a nucleobase containing polymer described herein was provided. Mouse mononucleosomal DNA in Tris-EDTA (TE) buffer (a blood mimic) was provided to the substrate. Compared to a control sponge treated with tetrahydrofuran (THF), the polymer-treated sponge retained significantly more DNA, as shown in FIG. 4: quantified by HS Qubit™, Thermofisher™.

The isolation of DNA from a flowing blood mimic using an embodiment of the invention is shown in FIG. 5. TE buffer treated with mouse mononucleosomal DNA was passed through a polyurethane sponge coated with a nucleobase containing polymer of the invention. After 30 minutes of cycling the blood mimic through the device at 28 mL/min at 37° C., the sponge was washed with PBS and the DNA eluted with elution buffer as discussed above (high salt buffer (>600 mM NaCl)). Compared to a control sponge treated with THF, the polymer-treated sponge coated with ms22 bound and eluted markedly more DNA from solution: quantified by HS Qubit™, Thermofisher™.

Example 5—Use of the Nucleobase Containing Polymers to Isolate DNA

FIG. 6 describes an extracorporeal device 210 application of a nucleobase containing polymer as described herein wherein the polymer is bound to a substrate 220. Whole blood 230 is removed from a subject 240 and provided to a system comprising a sampling loop 250 before being returned 260 to the subject. To the whole blood may be added an anticoagulant 270 to prevent blood clotting while it is extracorporeal. The sampling loop comprises the polymer bound to a substrate 220. The sampling loop further comprises a peristaltic pump 280, and bubble trap or traps 290. When whole blood passes through the substrate, cfDNA binds to the polymer and other whole blood components do not. When sufficient cfDNA has been bound to the polymer, the substrate is removed from the sampling loop 300. The substrate is suitably washed such that the cfDNA is retained while other blood components are removed from the substrate. The cfDNA is then eluted under suitable conditions to provide a concentrated sample of cfDNA for characterisation 310.

Example 6—Identification of Polymer Compositions and Elution Conditions

As shown in FIG. 7, several different polymer compositions with various concentrations and types of nucleobase- and non-nucleobase-containing side chain were produced and screened for DNA recovery from whole blood (pig) spiked with DNA ($^3$H-labelled chromatin: mouse mononucleosomal). Polyurethane sponges were used as substrates for the polymers, and each coated sponge was incubated in the spiked blood for 30 minutes at 37° C. The sponges were then removed from the spiked blood and washed with PBS before elution of the bound DNA from the polymers using an elution buffer consisting of 0.1 M sodium acetate, pH 5, 0.6 M NaCl, 0.15% Triton X-100 (EQ1 Buffer, Invitrogen™). The concentration of labelled DNA was quantified using liquid scintillation counting, and the comparative binding efficiencies of the polymers indicated in FIG. 10. Because the measured $^3$H signal can be influenced by the composition of the measurement solution, the results are represented as proportions of the signal measured from the quantity of DNA spiked into blood, in EQ1.

FIG. 9 identifies ms26 and ms28 as preferred embodiments of the invention due to their high retention and elution of DNA. FIG. 10 indicates compositions of polymers.

Various elution buffers were tested for their ability to release DNA from the polymers of the invention. Polyurethane sponges were coated with polymer of the invention in THF and each sponge was incubated in the whole blood (porcine) for 30 minutes at 37° C. The sponges were then removed from the whole blood and washed with PBS before elution of the bound DNA from the polymers using various elution buffers: EQ1, W8 or E4 (W8: 0.1 M sodium acetate, pH 5, 0.825 M NaCl, E4 buffer: 0.1 Tris-HCl, pH 8.5, 1.25 M NaCl). The concentration of labelled DNA was quantified using HS Qubit™, after purification using QIAamp Circulating Nucleix Acid Kit, and the comparative elution efficiencies of the elution buffers indicated in FIG. 8. A negative control sponge treated with THF was included for comparison, as well as a plasma control wherein isolated plasma (and thus concentrated cfDNA) was isolated and purified using QIAamp Circulating Nucleic Acid Kit,™. The results indicate that compared to the QIAamp kit, a comparable recovery method was established when elution is performed using high salt buffer as described herein. Plasma control generated by spinning test volume of blood (1 mL) at 2000 rcf for 10 min. The plasma supernatant was removed and made up to 1 mL with PBS before running on the QIAamp kit.

FIG. 8 indicates that a preferred elution buffer is one with a high salt concentration, and/or one with a high pH, for example 100 mM Tris-HCl pH 8.5, 1250 mM NaCl (high salt buffer with a NaCl concentration >600 mM).

Example 7—Binding of Nucleic Acids to Polymers

To identify whether polymers bound to and allowed isolation of circulating cfDNA from whole blood (which are typically 50-300 bp) as opposed to large DNA molecules (such as chromosomal DNA or DNA from leukocytes), polymers of the invention were prepared and coated onto polyurethane sponge while varying the composition of the polymers. These were provided to whole blood (human) spiked with mouse mononucleosomal chromatin, DNA was isolated and purified from the whole blood for 30 min at 37° C. incubation, PBS wash, elution with 100 mM Tris-HCl pH 8.5, 1250 mM NaCl (high salt buffer with a NaCl concentration >600 mM) and the DNA concentration of the eluted samples quantified by HS Qubit™ as shown in FIG. 9. The isolated DNA was then quantified by the addition of a fluorescent dye, DNA electrophoresis and optical densitometry using an Agilent™ Bioanalyzer™.

FIG. 9 indicates an embodiment of the invention for isolating short (50-300 bp) lengths of nucleic acids:—polymer designated ms26, which permitted not only a high recovery of DNA from whole blood (FIG. 9), but the DNA which it retained had the highest proportion of short DNA than any polymer tested.

The Bioanalyzer™ results of ms26 are shown in FIG. 11: (top) pure mouse mononucleosomal DNA, (middle) recovered DNA from polymer sponge, including small fragment mouse mononucleosomal DNA, (bottom) an untreated sponge lacking the polymer does not recover small fragment DNA.

Example 8—Haemocompatability Assay

It is beneficial that the polymers of the invention are haemocompatible (e.g. they cause minimal blood coagulation in use). This is particularly relevant for the use of the polymers of the invention as illustrated in FIG. 6. To that end, FIG. 13 indicates a qualitative coagulation assay using various polymers of the invention at different concentrations of coating solutions, where '+'=coagulation observable, and '−'=no evidence of coagulation.

FIG. 13 identifies msX as a preferred embodiment of the invention due to the improved haemocompatibility.

Example 9—MsX DNA Binding Assay

To identify whether polymer MsX bound and allowed the isolation of DNA, 125 mm$^3$ sponges treated with either MsX at 0.1% THF coating solution or THF coated, and their DNA binding ability was assayed using a flow-based setup. A solution of TE buffer spiked with 200 ng mononucleosomal DNA (160 bp) was incubated for 30 min at 37° C. with 1, 2 or 3 of the MsX or THF-treated sponges. These were then washed with PBS and bound DNA was eluted using 100 mM Tris-HCl pH 8.5, 1250 mM NaCl (high salt buffer with a NaCl concentration >600 mM). The DNA was quantified by HS Qubit™ (n=3, error bars show standard deviation) as shown in FIG. 14. The amount of DNA bound by each MsX sponge as shown in FIG. 14 is compared in FIG. 15.

Although the invention has been particularly shown and described with reference to particular examples, it will be understood by those skilled in the art that various changes in the form and details may be made therein without departing from the scope of the present invention.

The invention claimed is:
1. A method for the isolation of nucleic acids from a sample, the method comprising the steps of:
   (a) providing the sample comprising nucleic acids to be isolated to a nucleobase containing polymer wherein the polymer further comprises other positively charged moieties at physiological pH adapted to electrostatically interact with the nucleic acids to be isolated, and/or adapted to interact with the nucleic acids to be isolated via hydrogen bonding, and

(b) incubating at suitable conditions for binding the nucleic acids to be isolated to the polymer, followed by isolating the nucleic acids, comprising the following steps:

washing a complex formed between the nucleic acids to be isolated and the polymer by a wash buffer to remove one or more other components of the sample from the polymer while retaining the nucleic acids to be isolated on the polymer; and eluting the nucleic acids to be isolated from the polymer by an elution buffer wherein the elution buffer has an ionic strength selected from equivalent to or higher than that of 600 mM NaCl solution and optionally the elution buffer has a pH of 5 or higher.

2. The method of claim 1, wherein the nucleobase containing polymer comprises a polymer backbone with at least a proportion of side chains being nucleobase side chains selected from one or more of the following: adenine (A), cytosine (C), guanine (G), thymine (T), uracil (U) or a derivative thereof or combinations thereof, wherein the proportion of side chains of the polymer comprising the nucleobase is at least 1% but not more than 17%.

3. The method of claim 1, wherein the polymer comprises: (i) one or more monomers selected from the group consisting of 2 methoxyethyl acrylate, 2-methoxyethyl methacrylate, diethylamino ethylacrylate, diethylamino ethyl methacrylate, hydroxyethyl acrylate, hydroxyethyl methacrylate, methyl methacrylate, methyl acrylate, styrene, methyl styrene, glycidyl acrylate, glycidyl methacrylate, N-vinylacetamide, 2-methyl-2-nitropropyl methacrylate, acrylic acid, methacrylic acid, 2-[[(butylamino)carbo nyl]oxy] ethylacrylate, dimethylamino ethyl acrylate, dimethylamino ethyl methacrylate, mono-2-(acryloyloxy)ethyl succinate, poly (ethylene glycol) methyl ether acrylate/methacrylate and combinations thereof, and (ii) one or more (meth)acrylate-based monomers with nucleobase side chains selected from the group consisting of thymine ethylacrylate, thymine acetoxylethyl methacrylate, combinations thereof, and derivatives thereof.

4. The method of claim 3, wherein the polymer comprises: (i) one or more (meth)acrylate-based monomer selected from the group consisting of: 2 methoxyethyl acrylate (MEA), 2-methoxyethyl methacrylate (MEMA), diethylamino ethyl acrylate(DEAEA), diethylamino ethyl methacrylate (DEAEMA), poly(ethylene glycol) methyl ether acrylate (PEGA), poly(ethylene glycol) methyl ether methacrylate (PEGMA) and combinations thereof, and (ii) one or more other (meth)acrylate-based monomers with nucleobase side chains selected from a group consisting of thymine ethyl acrylate (ThEA), thymine acetoxylethyl methacrylate (ThAcMA), and combinations thereof.

5. The method of claim 3, wherein the polymer comprises: about 10-50% 2-methoxyethyl acrylate, about 0-50% 2-methoxyethyl methacrylate, about 1-40% diethylamino ethyl acrylate, about 1-25% poly(ethylene glycol) methyl ether acrylate, and about 1-17% thymine ethyl acrylate and/or thymine acetoxylethyl methacrylate.

6. The method of claim 5, wherein the polymer consists of about 0-50% 2-methoxyethyl methacrylate; about 1-40% diethylamino ethyl acrylate, about 10-50% 2 methoxyethyl acrylate, about 1-25% poly(ethylene glycol) methyl ether acrylate, and about 1-17% thymine ethyl acrylate and/or thymine acetoxylethyl methacrylate.

7. The method of claim 4, wherein the polymer corresponds to one of the following structures:

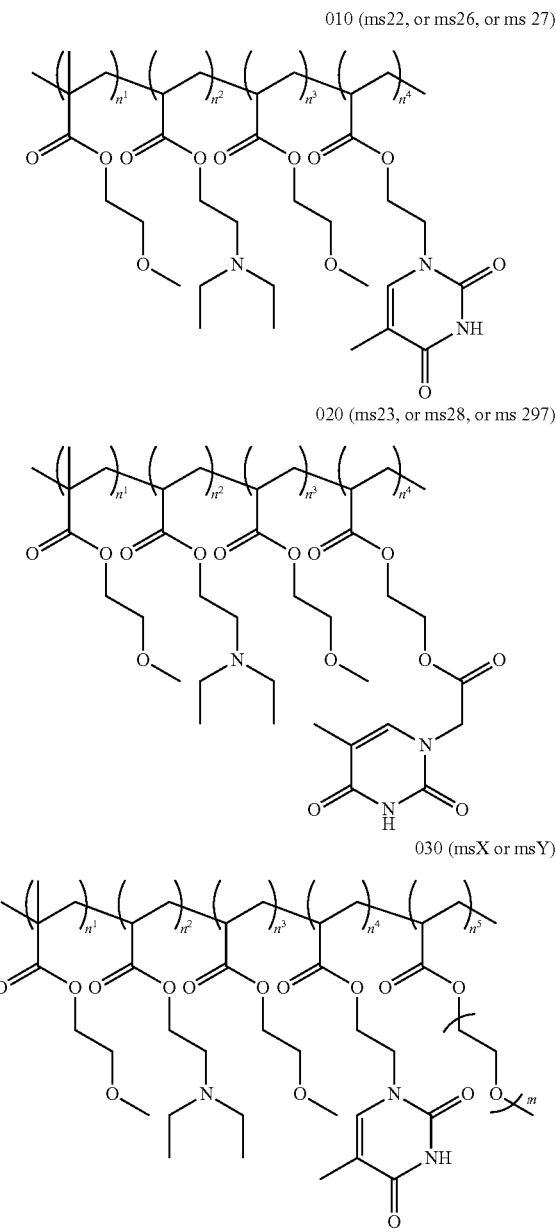

wherein m is between 1 and 50 and $n^1$, $n^2$, $n^3$, $n^4$, and $n^5$ are independently selected to provide a polymer with a composition as indicated in Table 1

|  | MEMA (%) | DEAEA (%) | MEA (%) | ThEA (%) | ThAcMA (%) | PEGA (%) |
|---|---|---|---|---|---|---|
| Ms13 | 39 | 32 | 29 | — | — | — |
| Ms22 | 38 | 27 | 29 | 6 | — | — |
| Ms23 | 37 | 26 | 28 | — | 9 | — |
| Ms26 | 42 | 25 | 32 | 1 | — | — |
| Ms27 | 38 | 26 | 28 | 8 | — | — |
| Ms28 | 39 | 28 | 29 | — | 4 | — |
| Ms29 | 33 | 28 | 25 | — | 14 | — |
| MsY | 39 | 30 | 29 | 1 | — | 1 |
| MsX | 47 | 15 | 36 | 1 | — | 1. | wherein
MEMA = 2-methoxyethyl methacrylate;

-continued

| MEMA (%) | DEAEA (%) | MEA (%) | ThEA (%) | ThAcMA (%) | PEGA (%) |
|---|---|---|---|---|---|

DEAEA = diethylaminoethyl acrylate;
MEA = 2- methoxyethyl acrylate;
PEGA = poly(ethylene glycol) methyl ether acrylate;
ThEA = thymine ethyl acrylate; and
ThAcMA = thymine acetoxyethyl methacrylate.

8. The method of claim 1, wherein the nucleic acid to be isolated is cfDNA.

9. The method of claim 1, wherein the elution buffer has an ionic strength equivalent to or higher than that of 1250 mM NaCl solution and/or the elution buffer has a pH of 8.5 or higher.

10. The method of claim 1, wherein the sample is a blood or serum or plasma sample.

11. The method of claim 1, wherein the method is part of an apheresis method.

12. The method of claim 1, wherein the polymer is provided on a solid substrate and the polymer comprises one or more (meth)acrylate-based monomers and one or more other (meth) acrylate-based monomers with nucleobase side chains.

13. The method of claim 12, wherein the one or more (meth)acrylate-based monomers are poly(ethylene glycol) methyl ether (meth)acrylates.

14. The method of claim 12, wherein the polymer comprises one or more (meth)acrylate-based monomers selected from the group consisting of MEA, DEAEA, MEMA, PEGA, PEGMA, DEAEMA and combinations thereof, and one or more other (meth)acrylate-based monomers with nucleobase side chains.

15. The method of claim 12, wherein the polymer consists of one or more (meth)acrylate-based monomers selected from the group consisting of MEA, DEAEA, MEMA, PEGA, PEGMA, DEAEMA and combinations thereof, and one or more other (meth)acrylate-based monomers with nucleobase side chains.

16. The method of claim 1, wherein the nucleic acids to be isolated are single stranded nucleic acids.

17. The method of claim 1, wherein the nucleic acids to be isolated are double stranded nucleic acids.

18. A method for the isolation of nucleic acids from a sample, the method comprising the steps of:
(a) providing the sample comprising nucleic acids to be isolated to a nucleobase containing polymer wherein the polymer further comprises other positively charged moieties at physiological pH adapted to electrostatically interact with the nucleic acids to be isolated, and/or adapted to interact with the nucleic acids to be isolated via hydrogen bonding, and
(b) incubating at suitable conditions for binding the nucleic acids to be isolated to the polymer, followed by isolating the nucleic acids,
wherein the nucleobase-containing polymer comprises:
(i) one or more monomers selected from the group consisting of 2-methoxyethyl acrylate, 2-methoxyethyl methacrylate, diethylamino ethylacrylate, diethylamino ethyl methacrylate, hydroxyethyl acrylate, hydroxyethyl methacrylate, methyl methacrylate, methyl acrylate, styrene, methyl styrene, glycidyl acrylate, glycidyl methacrylate, N-vinylacetamide, 2-methyl-2-nitropropyl methacrylate, acrylic acid, methacrylic acid, 2-[[(butylamino)carbonyl]oxy] ethylacrylate, dimethylamino ethyl acrylate, dimethylamino ethyl methacrylate, mono-2-(acryloyloxy)ethyl succinate, poly(ethylene glycol) methyl ether acrylate/methacrylate and combinations thereof, and (ii) one or more (meth) acrylate-based monomers with nucleobase side chains.

* * * * *